(12) United States Patent
Hibri

(10) Patent No.: US 11,679,017 B2
(45) Date of Patent: Jun. 20, 2023

(54) EXTERNAL PENILE PROSTHESIS FOR AUGMENTING MALE POTENCY

(71) Applicant: Spica Medical Technologies, LLC, San Antonio, TX (US)

(72) Inventor: Nadi S. Hibri, San Antonio, TX (US)

( * ) Notice: Subject to any disclaimer, the term of this patent is extended or adjusted under 35 U.S.C. 154(b) by 0 days.

(21) Appl. No.: 17/174,050

(22) Filed: Feb. 11, 2021

(65) Prior Publication Data

US 2021/0244562 A1  Aug. 12, 2021

Related U.S. Application Data

(60) Provisional application No. 62/975,112, filed on Feb. 11, 2020.

(51) Int. Cl.
*A61F 5/41* (2006.01)
*B29C 41/14* (2006.01)
*B29C 41/00* (2006.01)

(52) U.S. Cl.
CPC .............. *A61F 5/41* (2013.01); *B29C 41/003* (2013.01); *B29C 41/14* (2013.01); *A61F 2005/411* (2013.01)

(58) Field of Classification Search
CPC . A61F 5/41; A61F 2005/411; A61F 2005/414
See application file for complete search history.

(56) References Cited

U.S. PATENT DOCUMENTS

| | | | | |
|---|---|---|---|---|
| 2,581,114 A | * | 1/1952 | Larson | A61F 5/41 128/845 |
| 2,818,855 A | * | 1/1958 | Miller | A61F 5/41 600/41 |
| 4,429,689 A | * | 2/1984 | Yanong | A61F 5/41 600/39 |
| 5,243,968 A | * | 9/1993 | Byun | A61H 19/32 600/38 |
| 5,327,910 A | * | 7/1994 | Flynn | A61F 2/0054 600/38 |
| 5,344,389 A | * | 9/1994 | Walsdorf | A61F 5/41 600/39 |
| 5,695,444 A | * | 12/1997 | Chaney | A61F 5/41 600/38 |
| 5,951,460 A | * | 9/1999 | Vollrath | A61F 5/41 600/38 |

(Continued)

*Primary Examiner* — Samuel G Gilbert
(74) *Attorney, Agent, or Firm* — Gunn, Lee & Cave P.C.; Robert L. McRae

(57) ABSTRACT

An elastomeric device for improving the erection of the human penis may include a frustoconical collar sized to receive and snugly jacket the user's penis and apply effective pressure on the dorsal penile veins, and a radially extending pubic shield adapted to overlay the pubic area of the user. An elastic strap attached to the pubic shield may encircle the underside of the scrotum to apply effective pressure on the deep veins behind the scrotum and to retain the device on the user's penis during sexual activity. When used in combination with a conventional vacuum erection device, substantially airtight seals are established around the open end of the vacuum device, the base of the penis, and the anterior sealing surface of the pubic shield during evacuation pumping. Related methods are also described.

55 Claims, 20 Drawing Sheets

(56) References Cited

U.S. PATENT DOCUMENTS

| | | | | |
|---|---|---|---|---|
| 6,579,229 B1* | 6/2003 | Nan | ............... | A61F 5/41 |
| | | | | 600/38 |
| 6,749,558 B1* | 6/2004 | Brintle | ............ | A61F 5/41 |
| | | | | 600/38 |
| 2011/0275888 A1* | 11/2011 | Braud | ............. | A61F 5/41 |
| | | | | 600/39 |

* cited by examiner

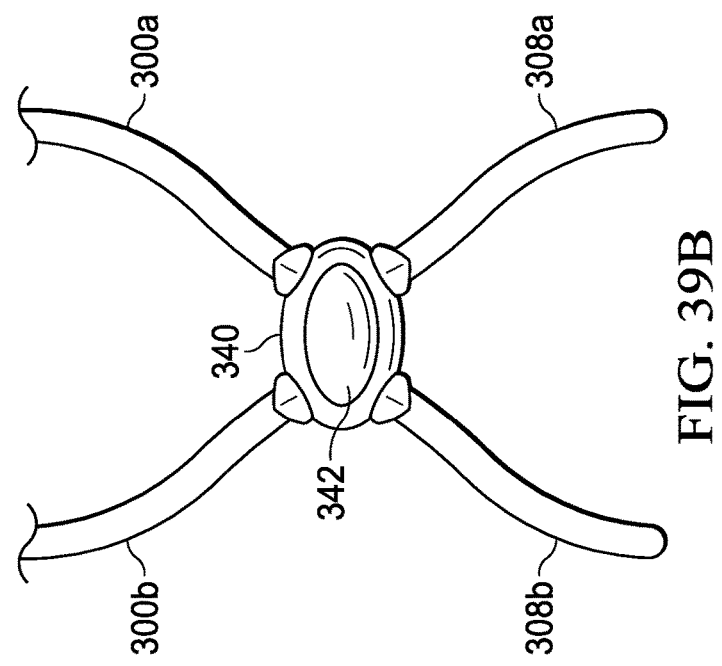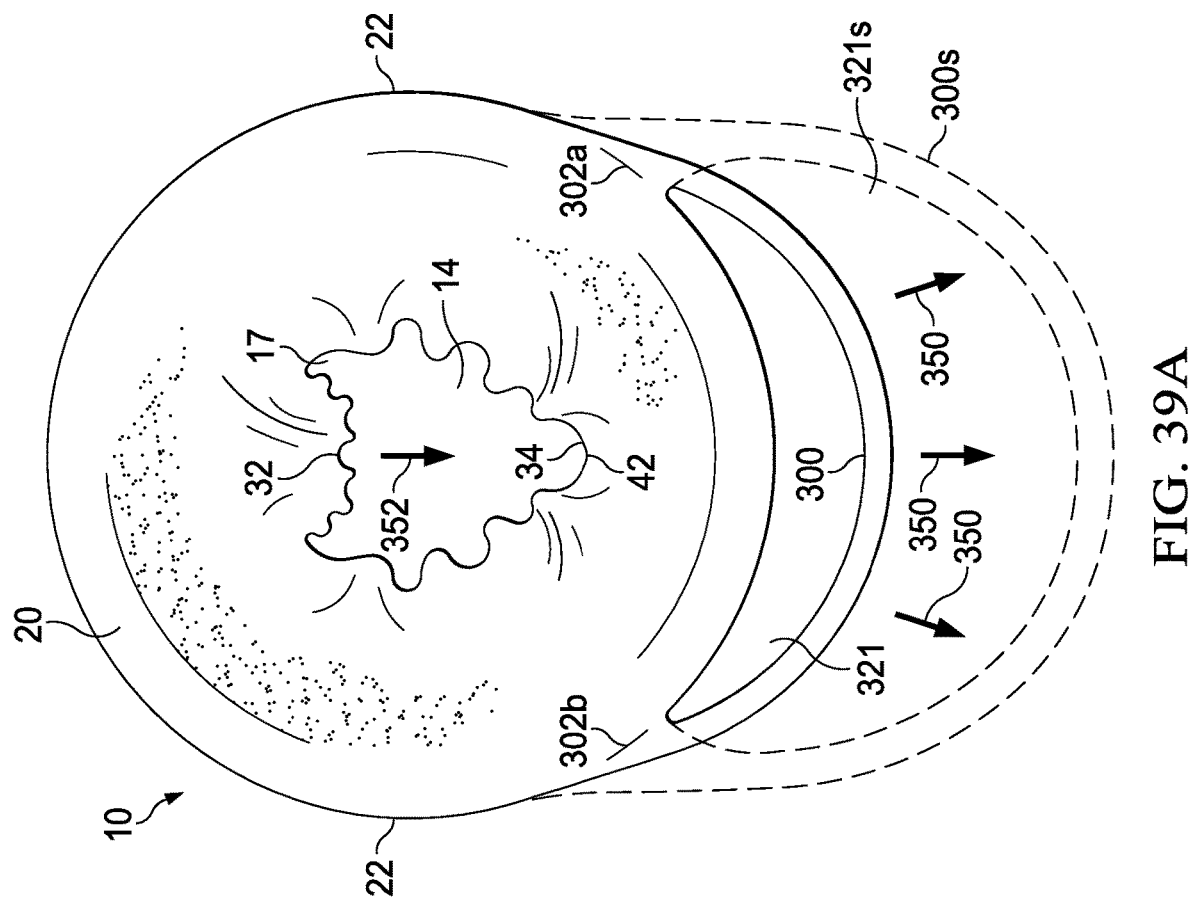

EXTERNAL PENILE PROSTHESIS FOR AUGMENTING MALE POTENCY

CROSS-REFERENCE TO RELATED APPLICATIONS

This is a non-provisional utility patent application Ser. No. 62/975,112, filed on Feb. 11, 2020, which is incorporated herein by reference.

FIELD

This disclosure relates to devices used in the noninvasive treatment of erectile dysfunction, and more particularly, to a constriction penile prosthesis, methods of making such prosthesis, and methods of using such prosthesis in combination with a vacuum erection device.

BACKGROUND

This section is intended to provide a background or context to the invention that is recited in the claims. The description herein may include concepts that could be pursued but are not necessarily ones that have been previously conceived or pursued. Therefore, unless otherwise indicated herein, what is described in this section is not prior art to the description and claims in this application and is not admitted to be prior art by inclusion in this section.

Erectile dysfunction (impotence) is the inability to get and keep an erection suitable for sexual intercourse. Erectile dysfunction, or ED, is the most common sex problem that men report to their doctor. Causes include medications, chronic illnesses, poor blood flow to the penis, or fatigue. Causes are usually medical but can also be psychological.

Most men have occasionally expressed some difficulty with their penis becoming hard or staying firm. However, ED is only considered a concern if satisfactory sexual performance has been impossible on a number of occasions for some time.

Men who have a problem with their sexual performance may be reluctant to talk with their doctor or friends, seeing it can be an embarrassing issue. Since the discovery that the drug Sildenafil, or Viagra™, effected penile erections, most people have become aware that ED is a treatable medical condition.

About one third of all grown-up men in the civilized world are more or less affected by this infirmity, especially those of middle or older age, but also more and more young men who are exposed to or susceptible to stress.

It is well known that ED may be the cause of various side effects such as alcoholism, heavy smoking, drug addiction, divorce, job problems, depression, brutality, racism, terrorism, and suicide. On the other hand, sexually content couples are more likely to keep themselves physically and mentally fit and have a positive outlook on life.

More than half of all physically induced cases of ED are associated with venous insufficiency of erectile tissues due to malfunction of venous swell pads and flaps which act as backflow valves. Most of these valves are in the dorsal penile veins and in the plexus of veins at the root of the penis behind the scrotum. About 30% of ED cases are caused by insufficient arterial blood supply due to arteriosclerotic obstruction or anti-hypertension medications.

External constriction devices have been provided which contract around the base of the flaccid penis and prevent the outflow of blood once the penis has risen into an erect state. Conventional constriction devices include several different styles. Examples of such devices include those disclosed in U.S. Pat. No. 1,608,806 issued Nov. 30, 1926 to Peter W. Nelson, and U.S. Pat. No. 4,872,462 issued Oct. 10, 1989 to Gilbert Salz. Such devices have not been successfully adopted for use with external erection devices.

The second category includes smaller, less cumbersome devices, known as constriction bands or rings which can be used alone or in combination with a vacuum erection device. Once an erection is achieved, the constriction device impedes the flow of blood from the penis, keeping it in an erect state. Such devices include U.S. Pat. No. 3,759,253 issued on Sep. 18, 1973 to Charles A. Cray and U.S. Pat. No. 4,539,980 issued on Sep. 10, 1985 to John L. Chaney. Such rings, usually consisting of elastic rubber, are strapped around the already erect penis. The pinch-off encompasses veins, arteries, and nerves, thus not only stopping the venous backflow which is desired, but also preventing the supply of fresh arterial blood. Shortly after the pinch-off, therefore, the penis becomes engorged and turns blue and numb, and the circumference where the ring is pinching the base of the penis starts to cause pain. The parts of the penis behind the pinch, around the scrotum, and in the perineum and at the penis root which are not pinched-off, turn limp so that the stiff front of the penis in front of the pinch-off is dangling down instead of erect. Accordingly, a normal coitus activity is not possible. Further, the ejaculate cannot escape through the choked off urethra but is emptied retrograde into the bladder.

Other constriction devices are available designed specifically for use with vacuum erection devices. Such constriction devices include a compression ring as disclosed in U.S. Pat. No. 1,225,341 issued on May 8, 1917 to Otto Lederer, a device with a short elastic sleeve as disclosed in Swiss Pat. No. 347,300 granted on Jun. 30, 1960 to Guiseppi Meldi, or an elastic sleeve with an expansible diaphragm as disclosed in U.S. Pat. No. 4,641,638 issued on Feb. 10, 1987 to Robert D. Perry.

Use of bands or rings with a vacuum erection device requires that either one ring or several bands, doubled or redoubled, be slipped over the open end of the plastic cylinder. Once the band or ring is in place around the end of the cylinder, the cylinder is slipped over the flaccid penis and pressed over the groin. In some devices, the closed end of the cylinder is flat or textured to permit it to be braced against a stationary structure to assist the user in holding the cylinder firmly against the pubic bone, thereby promoting a better seal around the open end of the cylinder and simultaneously freeing the hands of the user to connect and operate the vacuum pump. Once erection is achieved, the constriction ring or band is slipped off the open end of the cylinder, whereupon it contracts around the base of the erect penis.

Several drawbacks have been encountered through the use of conventional bands and rings, either alone or in combination with commercially available vacuum erection devices. Often, pubic skin or the scrotum can be sucked into the vacuum chamber causing pain or injury. Removal of the band can be painful and difficult.

Establishing an airtight seal around the open end of the vacuum cylinder during evacuation is also suboptimal, and the effectiveness of the existing vacuum cylinders for creating a satisfactory penile erection is significantly reduced primarily due to the lack of a seating surface adaptable to conform to the user's groin and the open end of the vacuum cylinder to provide an airtight seal.

A combination seal and constricting device has been described by Walsdorf et.al. in U.S. Pat. No. 5,344,389 issued Sep. 6, 1994. The subject device is made of a pliable elastomeric material and is characterized by a centrally disposed cylindrical collar connected at one end thereof to a radially extending skirt having a sealing surface.

The above described devices and prior art devices, in general, have insufficient means to adequately restrain venous backflow of all three main penile draining veins, the vena dorsalis superficialis, the vena dorsalis profunda penis at the top side of the penis, and the venae profundi penis at the underside of the penis behind the scrotum.

Albert G. Fischer in U.S. Pat. No. 5,439,007 issued Aug. 8, 1995 describes a suspensory for improving the erection of the human male penis including a rigid, generally rectangular ring composed of two crossbars and two sidebars, which, in use surrounds the penis as well as the scrotum.

There remains a need for an elastomeric, soft, and conformable external penile prosthesis and associated assembly that is easy to wear, remove, and provide a convenient, air-tight, and reliable seal, coordinated with a vacuum erection device. Further, the device should be effective in substantially compressing all three penile veins without inadvertently compressing the urethra, nerves, arteries, or skin.

SUMMARY

The present disclosure relates to the improved design and function over elastic rings, constriction bands, suspensories, external inflatable cuffs, and other constriction devices available for the external treatment of impotence. The disclosed device may be used alone or in combination with a vacuum erection device. The device may be used by men of normal potency to enhance their sexual pleasure, satisfy their partners, and to promote physiologic health of the user's genitourinary system and harmony between couples. Compared to existing therapies such as surgical implantation of a penile prosthesis or self-injection of vasoactive chemicals into the erectile tissues of the penis, the use of the present external penile prosthesis is harmless and inexpensive.

The design as provided focuses on the provision of a device that is user friendly, easy to handle, convenient to place and take off, reuse, and keep clean. In order to accomplish these objectives and others, the prosthesis may be provided in different sizes and may be configured to fit in an airtight fashion over the front opening of a vacuum erection tube.

In some embodiments, there is provided a penile prosthesis device having an elastic frustoconical collar designed to fit snugly around the base of the penis, and a radially extending pubic shield having a forwardly facing compressible sealing surface and a rearward facing seating surface that conforms to the user's pubis. According to some embodiments, a penile prosthesis as described herein is provided with a radially inwardly extending dorsal ridge that projects from the roof of the prosthesis collar and bears on the top of the penis, effectively compressing the superficial and deep penile veins and preventing backflow of the venous blood, without inadvertently compressing the penile arteries and nerves.

In contrast to constriction rings which cut off the venous return and engorgement of the penile veins and portion of the corpora cavernosa at the root of the penis behind the constriction zone so that the penile shaft dangles loosely between the thighs, a penile prosthesis as described herein may include a collar-flange structure which supports the erect penile shaft in a substantially 90-degree angle or other desired angle from the abdomen. Furthermore, the corpora cavernosa are protected from constriction by provision of a wide area of surface contact along the inner wall of the collar as described in more detail herein.

According to some embodiments of the invention, the bottom circumference of the collar may include a ventral recess sized and configured to accommodate the user's urethra at the underside of the penile shaft and thus allow normal antigrade ejaculation.

According to some embodiments of the invention, the lateral walls of the collar may include a plurality of longitudinal ribs and grooves sized and configured to increase the surface area of the central channel of the collar upon stretching of the collar. Further, the ribs and grooves may provide a conformal grip on the erect penis and prevent unwanted movement or slippage of the device during sexual activity.

In some embodiments, the invention further presents a penile prosthesis collar portion that provides elastomeric wall regions that are relatively more flexible and more distensible, and stretch more than the sidewall ribs, thus forming a dual modulus collar.

In further embodiments, any of the regions of variable thickness or variable hardness in the collar wall may produce a bending, twisting, or straightening movement of the collar upon active stretching.

In some embodiments of the present invention, an elongate resilient retention strap member is provided to secure the device during coitus. Both ends of the elastic strap are connected at connection points to the periphery of the pubic shield. Once the device is in place, the strap is stretched and placed behind the scrotum so that during coitus the device is retained on the penis. The deep penile veins at the underside surface at the root of the penis in the perineum behind the scrotum are simultaneously compressed by the strap to ensure that all the draining veins of the penis are adequately compressed.

Some embodiments describe fabrication and operation of a soft external penile prosthesis that includes a flexible body having a relatively firm pubic shield and a collar, each having a width, a diameter, a length, and a thickness. The flexible body may have a channel disposed within the collar, the channel defined by an upper wall and two sidewalls, wherein the upper wall includes a dorsal ridge that is strain limiting; and wherein the upper wall is positioned and arranged such that the sidewalls elastically stretch and expand to widen the channel to accommodate penile entry and/or expansion of the surrounding collar within a vacuum device. The two sidewalls converge inferiorly at a ventral recess configured to accommodate a user's urethra. The collar may be formed of elastic portions having different modulus of elasticity, so that during expansion of the collar, the modulus of elasticity of each portion at least partially controls the amount of expansion of each portion, thereby allowing the upper wall ridge to compress the penile dorsal veins, and allowing the lower wall to prevent compression of the urethra at the bottom of the channel. The penile prosthesis may be used in combination with a conventional vacuum erection device.

Still further, some exemplary embodiments provide a simplified method of penile erection actuation with a penile prosthesis/vacuum tube combination, which allows for convenient placement and taking off of the device, and establishing a substantially airtight seal around the open end of the vacuum tube and the base of the penis during evacuation pumping.

According to some embodiments, an external penile prosthesis of the present invention provides an improved airtight seal between the forwardly facing surface of the annular flange and the front edge of a conventional vacuum tube, avoiding the use of an adapter diaphragm and adapter insert, or other such mechanisms. Further, the cumbersome step of transferring a constriction band from the vacuum tube to the penis may be avoided.

In some embodiments, an external penile prosthesis may be adapted for use in the treatment of erectile dysfunction of a user, the user having a pubis, a scrotum, and a penis including a shaft, a base of the shaft, a top side, an underside, a glans, a urethra, a superficial dorsal vein, a deep dorsal vein, arteries, nerves, corpora cavernosa, and corpus spongiosum, the prosthesis including: a collar having a central channel that is contractible to accommodate the user's penis in a flaccid state and expandable to accommodate the user's penis in an erect state, the central channel including a dorsal ridge and a ventral recess; and a pubic shield extending radially from the collar at a proximal end of the collar, the shield having a rearward facing surface conformable to the user's pubis; wherein the dorsal ridge is configured to reversibly compress the superficial dorsal vein and the deep dorsal vein of the penis and substantially avoid compression of the arteries and nerves; and wherein the ventral recess is configured to substantially avoid compression of the urethra.

In some embodiments, a method of fabricating an elastomeric penile prosthesis may include molding a penile prosthesis assembly including a shield and a collar in a single, integral, unitary piece from different pieces of thermoset compatible silicone rubber, the prosthesis including rearward and inner portions formed from a less elastic silicone rubber than forward and outer portions of the prosthesis, the shield and the collar being molded to form a smooth, shoulderless external surface and a textured internal surface.

In some embodiments, a method of fabricating an external penile prosthesis having a collar and a shield may include providing a mold core having a configuration corresponding to a shape of a central passageway of the collar; providing a polymeric insert in the form of a prefabricated dorsal ridge receivable within a corresponding concavity of the mold core; providing a polymeric insert in the form of a prefabricated ventral sulcus wall receivable overlying a corresponding convexity of the mold core; dip molding an inner layer of the collar and a rearward layer of the shield; allowing the layers to cure; dip molding a front layer of the shield; allowing the layers to cure at room temperature or inside an oven into a single, fused, integral piece of elastomeric rubber; and removing the mold core from the integral piece of elastomeric rubber.

In some embodiments, a method of fabricating a penile prosthesis may include providing an outer mold having a mold cavity of generally an outer configuration of the prosthesis and having a surface texture desired for the prosthesis; providing a mold core receivable within the mold cavity, the mold core and the mold cavity being sized and configured to define inner and outer configurations and surface features of the prosthesis; inserting dorsal ridge and ventral sulcus wall members about the mold core; enclosing the mold core and parisons within the outer mold; and filling remaining portions of the mold cavity with another parison of liquid silicone rubber by injection molding, which, when molded and cured, will display a selected degree of elasticity and hardness.

In some embodiments, a method of using a penile prosthesis as described herein with a vacuum erection device which comprises a vacuum cylinder with an open end, the shield of the prosthesis having a forward-facing sealing surface, the collar of the prosthesis having a funnel-like front aperture, may include placing the penile prosthesis over the open end of the vacuum cylinder so that the sealing surface of the shield rests flush against the open end of the vacuum cylinder thereby forming an airtight seal between the shield and the vacuum cylinder; placing the user's flaccid penis into the funnel-like front aperture of the penile prosthesis thereby creating a seal between the user's penis and the penile prosthesis; operating the vacuum erection device to draw the penis into the cylinder; further activating the vacuum within the cylinder gradually while the user performs Kegel or pelvic contraction exercises until the penis is in the desired erect state; pressing the vacuum cylinder against the pubic shield, driving the shield towards the user's groin, stabilizing the root of the penis and driving the user's penis forward and deeper into the cylinder, thus maximizing erection of the penis; releasing the vacuum within the cylinder; and removing the erect penis from the cylinder with the prosthesis disposed about the penis.

Other objects, advantages, and novel features of the invention will become apparent from the following detailed description of the invention when considered in conjunction with the accompanying drawings.

BRIEF DESCRIPTION OF THE DRAWINGS

The invention can be better understood with reference to the following drawings and description. The components in the figures are not necessarily to scale, emphasis instead being placed upon illustrating the principle of the invention. Moreover, in the figures, like referenced numerals designate corresponding parts throughout the different views.

FIG. 39A is a front elevation view of the rearward facing surface of a penile prosthesis according to one embodiment of the invention depicting a retention strap that is integrally molded with the rest of the pubic shield portion of the device.

FIG. 39B is a perspective view of the distal portions of two strap segments that may be attached to the rest of the penile prosthesis. The strap segments are joined together by a strap buckle.

DETAILED DESCRIPTION

Figure 1:
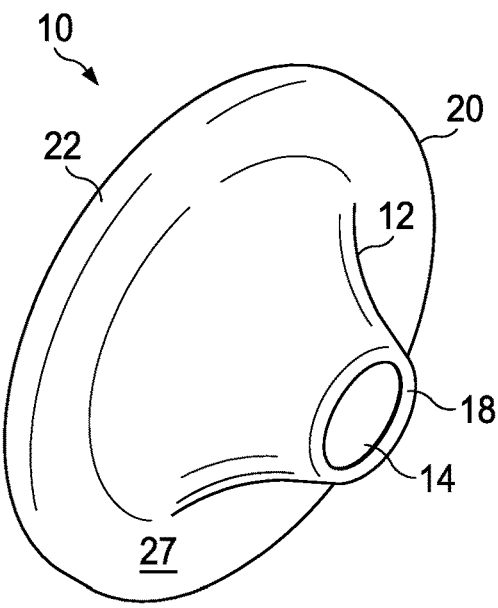
FIG. 1 is a front perspective view of the forward-facing surface of a penile prosthesis depicting a frustoconical collar and a radially extending pubic shield or flange portion.
Figure 2:
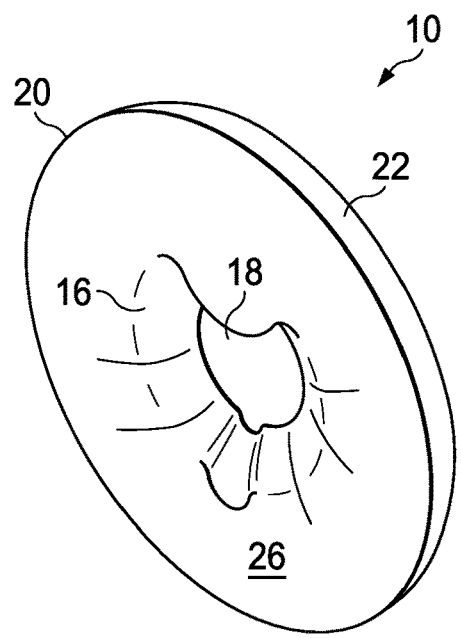
FIG. 2 is a rear perspective view of the rearward facing surface of the penile prosthesis of FIG. 1 depicting the funnel-like aperture of the frustoconical collar.

As shown in FIGS. 1-5, for example, an external penile prosthesis 10 may include a frustoconical collar 12 defining a central channel 14 therethrough having a relatively wider proximal opening 16 and a relatively narrower distal opening 18. The proximal opening 16 may be positioned nearer to the user's pubic region when using the prosthesis 10, and the distal opening 18 may be positioned further from the user's pubic region. A radially extending flange or pubic shield 20 may be substantially concentrically disposed around collar 12 and may be molded to have a substantially uniform thickness from the edge 22 of pubic shield 20 to the proximal opening 16 of channel 14 thereof. The pubic shield 20 may transition to the collar 12 via a smooth shoulder 24. The collar 12 may feather inwardly toward the distal opening 18 to a fairly thin dimension. Pubic shield 20 has an outer surface 27 and is preferably flexible and provides a smooth seating inner surface 26 that retains the penile prosthesis 10 despite movements of the user during coitus. Edge 22 of pubic shield 20 may be easily grasped by the user during application to or removal from the penis 50. In some embodiments, shield 20 may have a uniform thickness of about 7-8 mm, for example, but any suitable thickness may be used, and such thickness may or may not be uniform. In some embodiments, shield 20 may be substantially circular and may have a diameter of about 60-80 mm, for example, but other suitable sizes and shapes may be used. In some embodiments, in an unexpanded state, shield 20 may extend radially about 20 mm from collar 12 to edge 22.

The collar 12 may have a smooth, tapered, leading end 30 to guard against irritation or erosion of a sexual partner's tissues. A trailing portion of collar 12 may merge into a central portion of shield 20 forming the proximal opening 16 such that collar 12 may be shaped like a funnel and may be substantially trefoil or ovoid in cross-section. The wall thickness of collar 12 at the proximal opening 16 may be around 3 mm, for example, and may gradually become thinner towards distal opening 18. Of course, any suitable thickness may be used, and the thickness may or may not be tapered. In some embodiments, when collar 12 is in its relaxed, unexpanded state, it may have an outside diameter at its proximal end of about 3.5 cm and an outside diameter at its distal end of about 2.5 cm, an inside proximal diameter of about 3.0 cm, and an inside distal diameter of about 2 cm, for example. The collar 12 may extend substantially perpendicularly outward from pubic shield 20 to a distance about 2.5 cm, for example. In some embodiments, collar 12 may have a length ranging from about 25 mm to about 50 mm and an unexpanded outer diameter ranging from about 20 mm to about 35 mm. In some embodiments, channel 14 may have an unexpanded proximal diameter of about 30-40 mm and an unexpanded distal diameter of about 17-22 mm, for example. In some embodiments, collar 12 may have an unexpanded length and an unexpanded outer diameter wherein the unexpanded length ranges from about 1.2 to about 1.7 times the unexpanded outer diameter. In some embodiments, collar 12 may have an unexpanded length and an unexpanded outer diameter wherein the unexpanded length and the unexpanded outer diameter are about equal. Of course, any suitable dimensions and proportions may be used.

In some embodiments, as shown in FIGS. 1-4, for example, collar 12 and the openings 16, 18 may be centrally disposed relative to the edge 22, which may have a diameter of about 8 cm, for example. The thickness of pubic shield 20 may be about 0.8 cm, for example. The thickness of the sidewall of the collar 12 may proximally be about 5 mm and may distally be about 3.5 mm. It should be understood that such dimensions and proportions may vary as penile prosthesis 10 is provided in different sizes. Further, the measurements may be varied according to factors such as, for example, the hardness or modulus of elasticity of the material used in making penile prosthesis 10. The opening 18 of collar 12 should be expandable to accommodate a maximum diameter of the shaft of an erect penis of a particular patient.

Referring again to FIGS. 1-5, opening 18 of collar 12 may have a minimum diameter when in its relaxed, unexpanded state that is slightly smaller than the diameter of a flaccid penis 50 with which it is used, but stretchable enough to accommodate the erect penis 50 to avoid undue constriction. It is believed that most adult erect penises can be accommodated with a limited number of properly sized prostheses having a range of collars 12 and openings 16, 18 of differing diameters, that may, for example, be labeled as small, medium, and large to best accommodate the penis size of a particular user.

Figure 3:
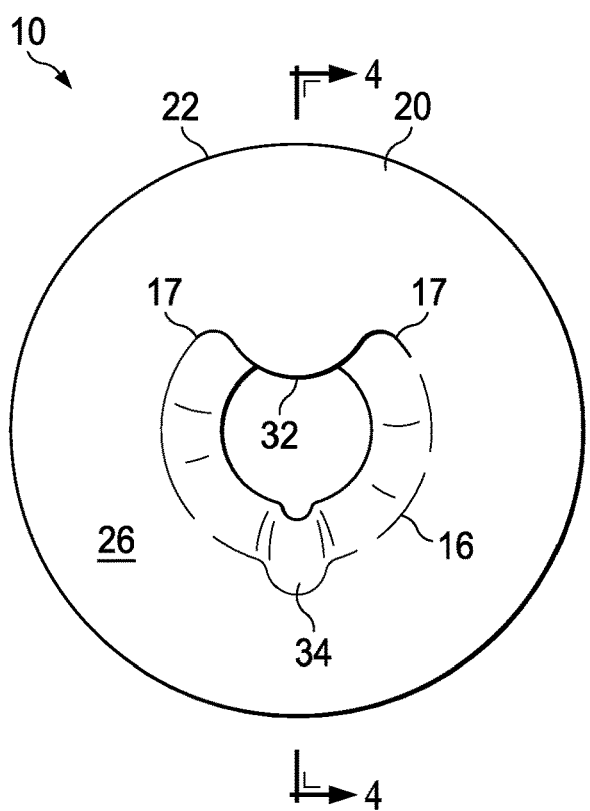
FIG. 3 is a rear elevation view of the rearward facing surface of the penile prosthesis of FIG. 1 depicting a dorsal ridge projecting inwardly from the roof of the channel within the frustoconical collar of the penile prosthesis. Note the ventral recess.
Figure 4:
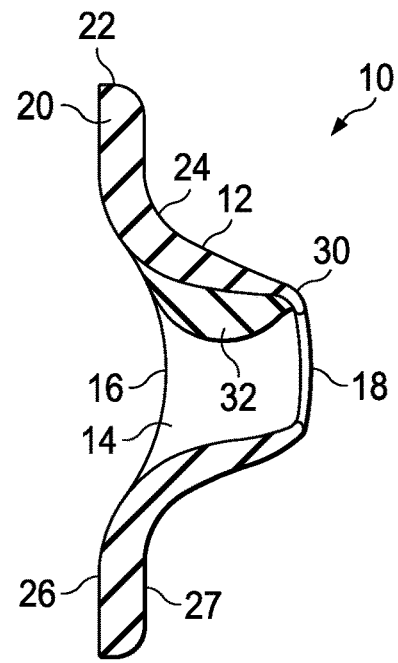
FIG. 4 is a cross-sectional view of the penile prosthesis of FIG. 1 taken along a mid-longitudinal plane 4-4 as shown in FIG. 3.
Figure 5:
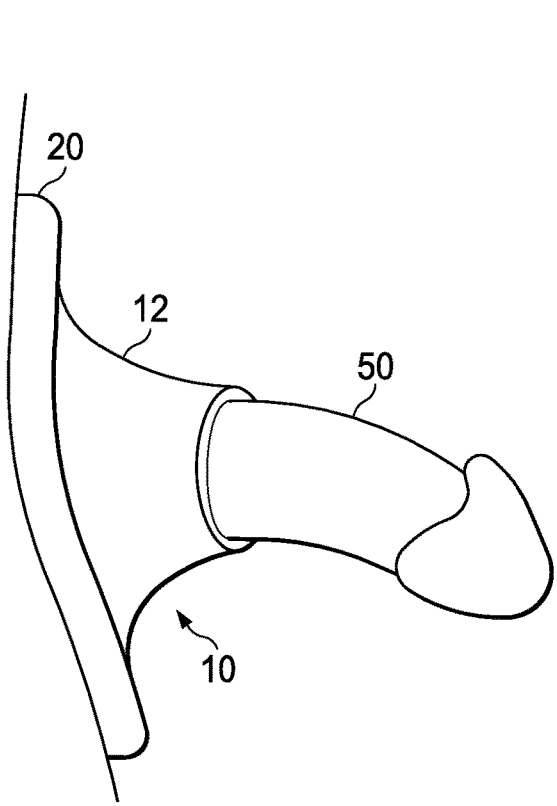
FIG. 5 is a simplified side elevation view of the penile prosthesis of FIG. 1 after it has been placed over a semi-flaccid penis, before attaining a full erection.
Figure 6:
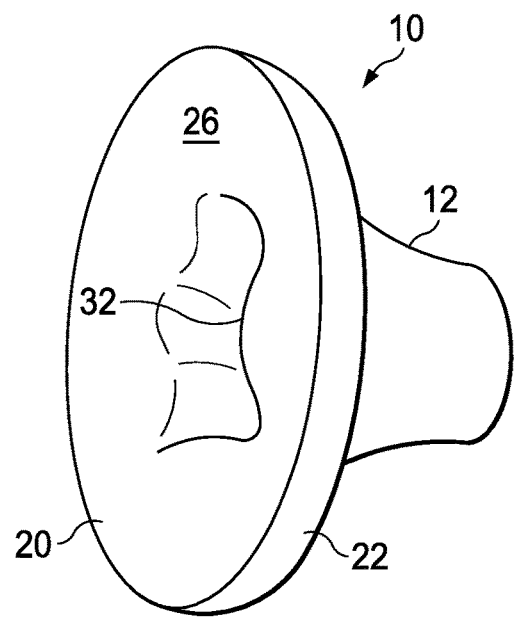
FIGS. 6 and 7 are oblique perspective views of the rearward facing aspect of the penile prosthesis of FIG. 1.
Figure 7:
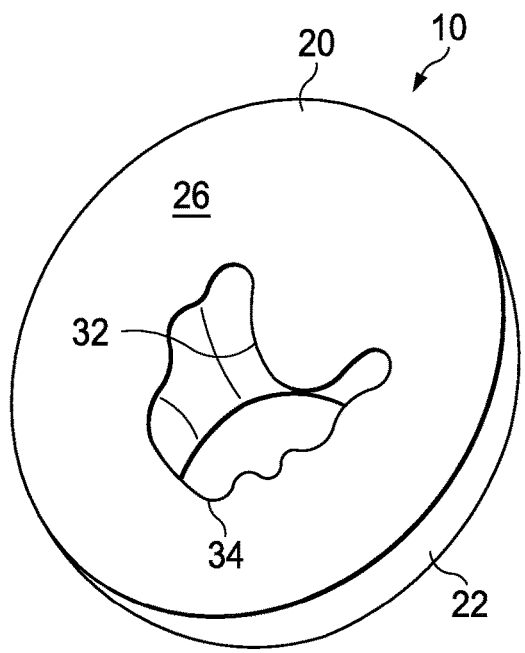

Referring now to FIGS. 3 and 4, as shown projecting inwardly from the inner roof of channel 14, the collar 12 may include a dorsal ridge 32 which, when the device is in use, bears on the top of the penis tissue to minimize or prevent outflow of venous blood from the penis 50. Desirably, in some embodiments dorsal ridge 32 may be substantially wedge-shaped and may compress a surface area of the penis 50 which is wide enough to accommodate anatomical variations in the positions of the superficial and deep dorsal penile veins, and dorsal ridge 32 may be smoothly rounded to be comfortable to the wearer. In some embodiments, dorsal ridge 32 may be ribbed or otherwise shaped to prevent slippage. In some embodiments, dorsal ridge 32 may be provided in a contrasting color to the rest of the collar 12 to facilitate visual identification of the ridge during use and to insure proper placement of the dorsal ridge 32 at the dorsum of the user's penis. By positioning dorsal ridge 32 substantially in the midline extending from the upper margin of proximal opening 16 close to the user's pubis and anteriorly to the level of leading end 30, steady and firm compression to the deep dorsal veins may be maintained, regardless of sexual activity. Since dorsal ridge 32 is essentially wedge-shaped, it exerts maximal pressure in the midline, where the dorsal penile veins are located, and displaces the dorsal arteries and nerves, which extend parallel to the veins sideways into the relatively wider dorsolateral recesses 17 of channel 14.

In some embodiments, the collar 12 may be integrally formed with the pubic shield 20 and the dorsal ridge 32, and together they may provide a versatile penile erection augmentation prosthesis that can accommodate the size of a particular penis at different stages of erection. As the penis sizes may vary significantly, it may be advisable to maintain an inventory of different sized devices to address all users and conditions. While functional, the need to maintain and manufacture an inventory of devices with different sizes, moduli of elasticity, and hardness may be reduced to a practical minimum. In practice, a particular patient may be provided with at least two different devices to try at the outset. Smaller or larger devices as well as other devices of lesser or greater elasticity may be provided to the user as desired. For example, such personalized attention may be provided by a professional who is familiar with the issues of erectile dysfunction as well as the different options available for its treatment.

Figure 8:
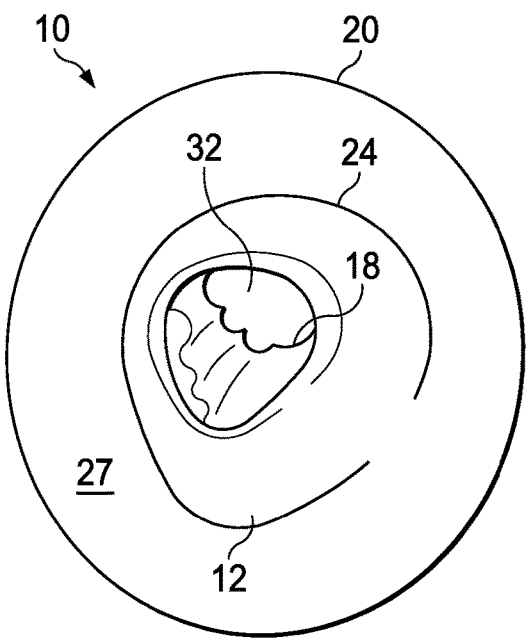
FIGS. 8 and 9 are oblique perspective views of the front facing aspect of the penile prosthesis of FIG. 1 depicting a trefoil configuration of the collar.
Figure 9:
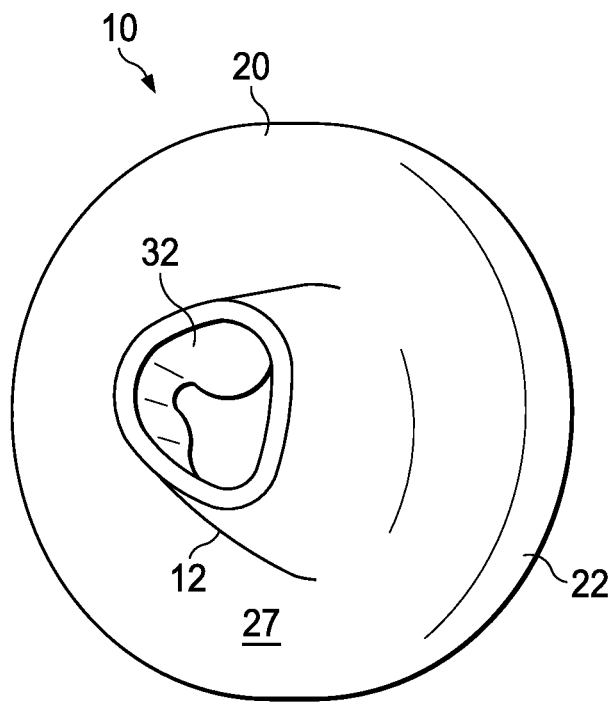
Figure 10:
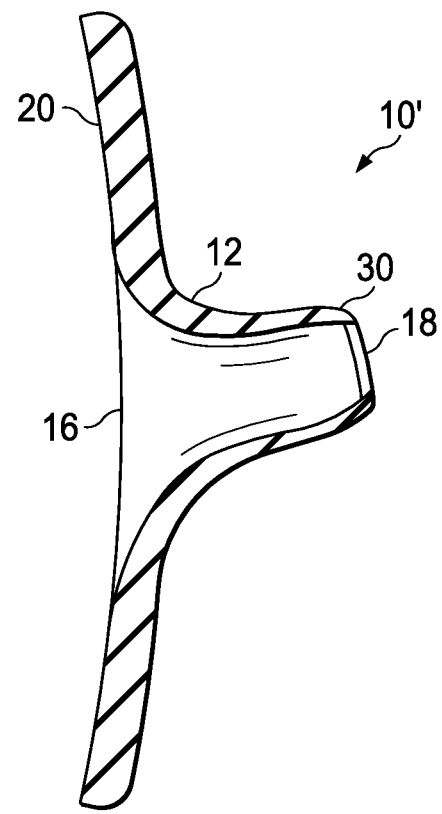
FIG. 10 is a cross-sectional view of another embodiment of a penile prosthesis depicting one possible variation in the shape, configuration, and proportions of the different elements of the penile prosthesis.

FIGS. 6-9 provide various perspective views of the penile prosthesis 10 to better illustrate some advantageous features of some embodiments of the prosthesis. Although the exemplary penile prosthesis 10 of FIGS. 6-9 depicts the shield 20 and the collar 12 in certain shapes prior to deployment, one of ordinary skill in the art will recognize that the present invention is not so limited. By changing the shape of the body of penile prosthesis 10, or the size, position, or configuration of the collar 12 and shield 20, different sizes, shapes, and configurations may be achieved. For example, as shown in FIG. 10, an embodiment of penile prosthesis 10' is shown having a collar 12 that is off-center with respect to shield 20 and disposed at a non-perpendicular angle with respect to shield 20, such that prosthesis 10' would direct a user's penis slightly upward, for example. Thus, an individual penile prosthesis 10 can be scalable in size and shape by replacing one component with another. For example, although the exemplary collar 12 shown in FIGS. 8 and 9 is depicted as frustoconical in the longitudinal direction and trefoil in cross-section when unexpanded, one of ordinary skill in the art will recognize that other configurations are possible. By changing the shape of collar 12, various functional properties may be enhanced or modified.

Figure 11:
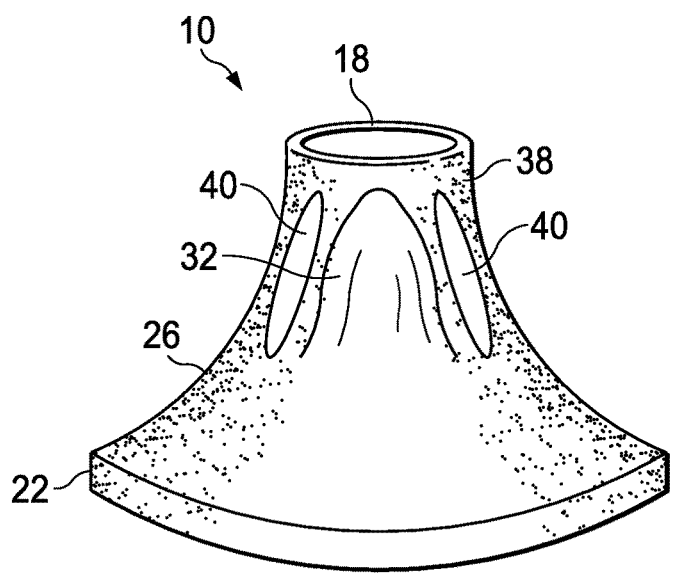
FIG. 11 is a perspective view of a penile prosthesis turned inside-out depicting the roof ridge and two sidewall ridges.
Figure 12:
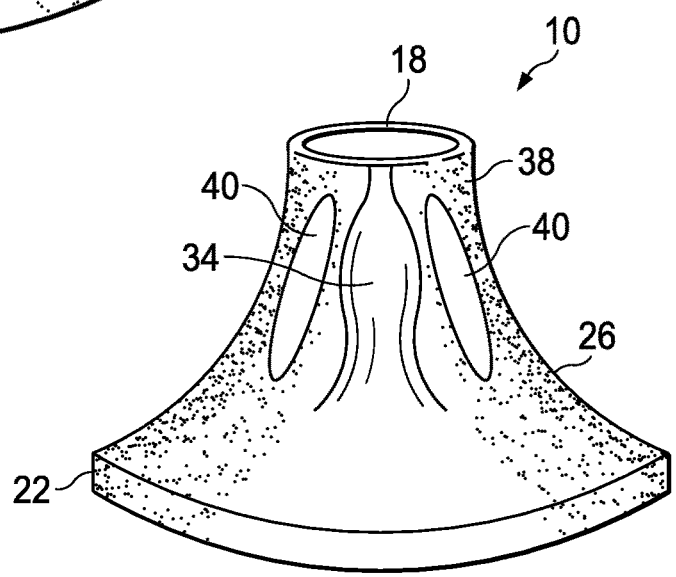
FIG. 12 is a perspective view of a penile prosthesis turned inside-out depicting the ventral urethral recess and two side ridges.
Figure 13:
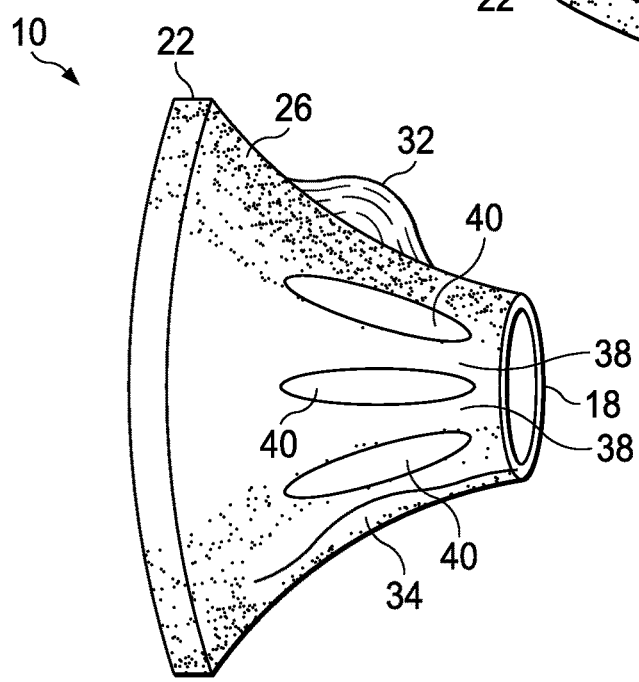
FIG. 13 is a perspective view of a penile prosthesis turned inside out depicting features of a sidewall including three arcuate sidewall ribs. Note the dorsal ridge and the ventral recess at the upper and lower margins of the figure.
Figure 14A:
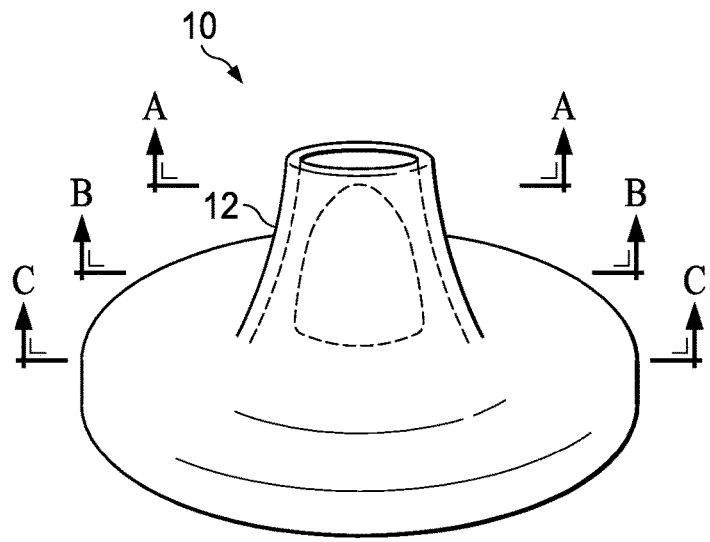
FIG. 14A is a front perspective view of a penile prosthesis showing in dotted line the dorsal ridge within the collar.

Turning now to FIGS. 11, 12, and 13, penile prosthesis 10 may be turned inside out by the user to enable thorough washing of the device after use. As shown in FIG. 11, features at the top surface of channel 14 and visible when the prosthesis 10 is turned inside out may include dorsal ridge 32 with partial visualization of a pair of superior lateral wall ribs 38 (further shown in FIG. 16 and FIG. 17) on each side of dorsal ridge 32.

FIG. 12 demonstrates features of penile prosthesis 10 oriented so as to view the ventral portion of channel 14, mainly a ventral recess 34, with partial visualization of inferior lateral wall grooves 40 (refer also to FIG. 16 and FIG. 17) on each side of ventral recess 34.

The viewed inner surface 26 of shield 20 is shown to better advantage in FIGS. 11, 12, and 13, and is optionally smoothly textured to provide comfort to the user and improved wettability of the inner wall of collar 12 as it slides against the user's skin.

Figure 15:
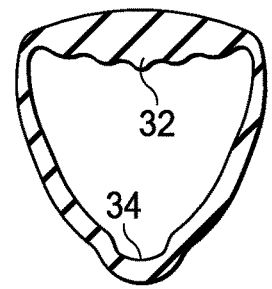
FIG. 15 is a cross-sectional view of the collar in FIGS. 14A and 14B taken along the line A-A, showing the anterior portions of the dorsal ridge and the ventral urethral recess.
Figure 14B:
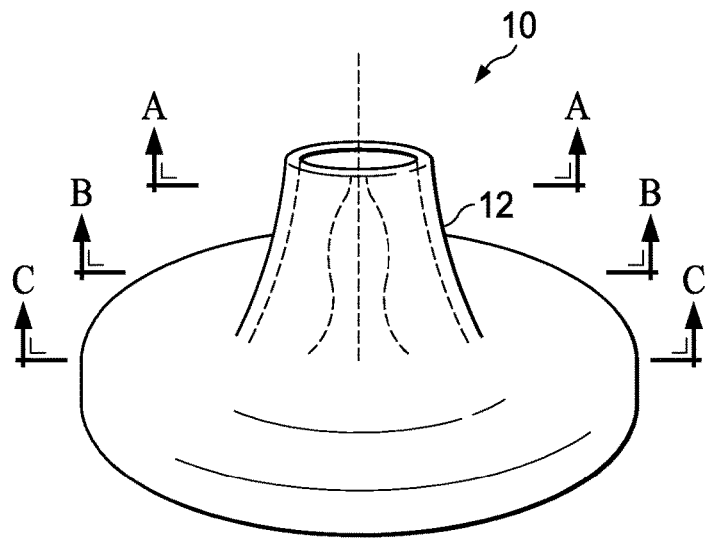
FIG. 14B is a front perspective view of a penile prosthesis showing in dotted line the ventral urethral recess within the collar.
Figure 16:
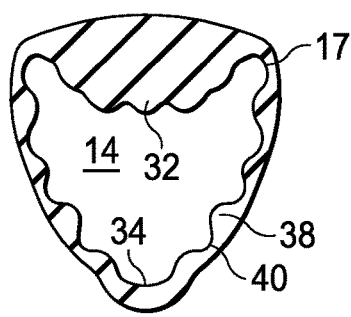
FIG. 16 is a cross-sectional view of the collar in FIGS. 14A and 14B taken along the line B-B, showing the dorsal ridge and ventral urethral recess as well as the sidewall ridges.
Figure 17:
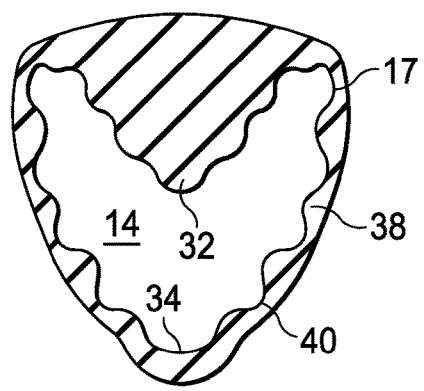
FIG. 17 is a cross-sectional view of the collar of FIGS. 14A and 14B taken along the line C-C.
Figure 19:
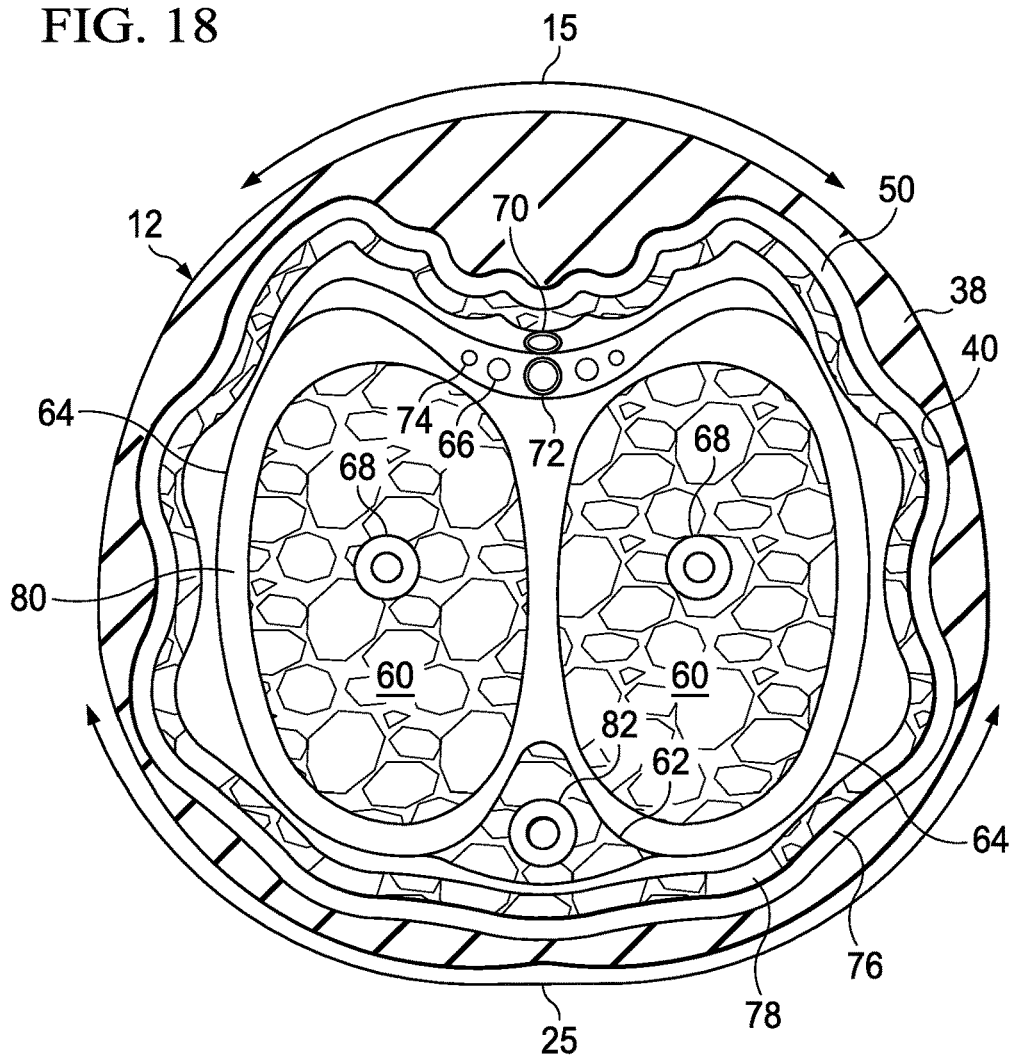
FIG. 19 is an anatomical cross-sectional view of a penile shaft disposed within the penile prosthesis shown in FIG. 18 depicting compression of the dorsal superficial and deep penile veins. Note that the urethra within the corpus spongiosus has been spared from compression due to the stretching of the ventral portion of the prosthesis along the ventral urethral recess.
Figure 21:
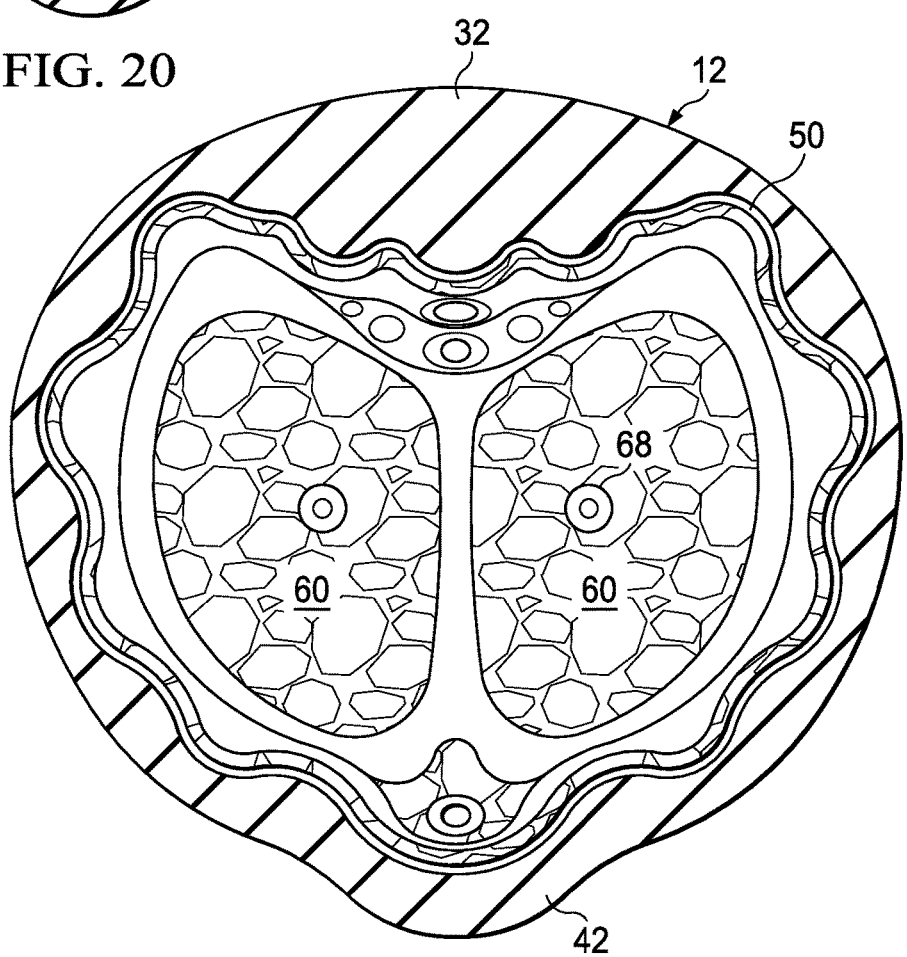
FIG. 21 is an anatomical cross-sectional view of an erect penile shaft disposed within the penile prosthesis shown in FIG. 20 depicting lateral stretching of the ventral recess wall whereby the recess is widened whereas the sidewalls are stretched and bowed outwardly by expansion of the erect penis, avoiding compression of the corpus spongiosus and the urethra.

Referring now to FIGS. 14A-17, there are shown embodiments of cross-sections of collar 12 of penile prosthesis 10. In some embodiments, collar 12 may comprise at least two materials possessing different hardness and elastic moduli. In some embodiments, the collar 12 may have a substantially trefoil or triangular cross-sectional configuration, with the dorsal ridge 32 forming a top sidewall, and two sidewalls converging towards the ventral recess 34. As shown in FIG. 16 and FIG. 17, the sidewalls may be formed of a plurality of lateral wall ribs 38 and lateral wall grooves 40 that enclose channel 14 of collar 12. Alternatively, as shown in FIG. 15, the sidewalls may be substantially smooth. The outer surface of collar 12 may be smooth, such as may define a shoulderless construction. The dorsal ridge 32 may be thicker than other regions of the collar 12 and therefore substantially less elastic than the rest of the collar. The plurality of lateral wall ribs 38 may press against the lateral walls of the base of the penile shaft while the plurality of lateral wall grooves 40 therebetween become flattened and elongated in response to circumferential stretching of the collar 12 by the expanding penile shaft as shown in FIGS. 19 and 21, for example. As the collar sidewalls are stretched and displaced radially outward, the dorsal ridge 32 may be depressed inwardly thus applying downward pressure upon the penis that is sufficient to restrict the flow of blood through the dorsal veins. Blood being supplied to the penis by the arteries may thus be maintained and retained in the erectile tissue of the organ "corpora cavernosa" to cause and maintain penile erection.

Referring now to FIGS. 18-21, the circumference of channel 14 prior to penis entry and enlargement of channel 14 (shown in FIGS. 18 and 20) may be substantially less than the circumference of the penis during arousal as shown in FIGS. 19 and 21, so that the aroused penis, especially when erection is induced sufficiently as within a vacuum device, will exert a biasing force on the inner walls of collar 12 when the prosthesis 10 is mounted upon the penis. In practice, if used with a vacuum tube 200 (see, e.g., FIGS. 36, 37, 41), a flaccid penis may be drawn into channel 14 by vacuum pressure within vacuum tube 200, and the corpora cavernosa 60 may become engorged with blood, stretching the tunica albuginea 80, thus increasing the stiffness of the penis 50, including the root 56 of the penis 50 within collar 12, and the collar sidewalls are stretched and the channel 14 is expanded. Collar 12, being disposed around the base of the penis 50, is expanded and becomes more rigid. The top region of collar 12 may flatten slightly and may be drawn downward into increased pressure contact against a dorsal region of the penis 50 as illustrated in FIGS. 19 and 21.

In some embodiments, the dorsal ridge 32 may be integrally formed with the pubic shield 20 and should be sufficiently firm to effectively press onto the penile dorsum to restrict the flow of venous blood in the dorsal veins. Advantageously, the substantial wedge-shape of the dorsal ridge 32 serves to distract the dorsal penile arteries 74 and penile nerves 66 laterally outward thus avoiding inadvertent interference with arterial blood flow or injury to the penile nerves 66.

With reference to FIG. 1, for example, in some embodiments, the various parts of prosthesis 10 may be made from the same elastomeric material. Various functional properties may be engineered by controlling the relative thicknesses of the component walls, so as to obtain regions of higher and lower stiffness. In homogenous elastomers, regions of lower stiffness are those defined by the thinnest walls (e.g., by the portions with the lowest resistance to stretching). Expansion and stretching in these regions may further thin the walls and may increase the volume of channel 14 in these regions. To accommodate the asymmetric elongation of two opposite walls of channel 14, the penile tissues within the expanding volume may bend to some degree. Upon expansion of the user's penis by evacuation pumping in a vacuum chamber, for example, an asymmetrical or differential biasing counterforce may be configured to cause the prosthesis 10 to bend the user's penis with respect to the axis of channel 14 to correct deformity and/or annoying angulation if needed.

In some embodiments, more than one elastomeric material may be used in making the prosthesis 10. For example, materials having a high elastic modulus may be used for portions of the prosthesis 10 where expansion or stretching is undesirable, while materials having a low elastic modulus may be used for portions of the prosthesis 10 where extensibility is desired. Upon active stretching of the collar 12 by the penis 50 undergoing erection and enlargement, either spontaneously or by creating a vacuum in a vacuum device, the stretching of the collar 12 is accommodated by bending of the collar 12 around the stiffer limiting layer at the top side of the collar 12 or selectively along the sidewalls, for example.

Figure 18:
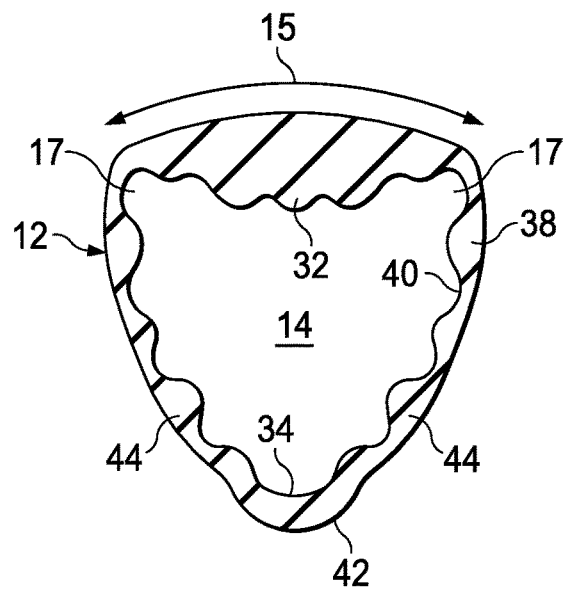
FIG. 18 is an enlarged cross-sectional view of the collar of FIGS. 14A and 14B similar to FIG. 17 showing a ventral recess wall that is relatively thin.

With further reference to FIG. 18, in some embodiments, the cross-sectional configuration of collar 12 may be trefoil or triangular in shape. Upon expansion of channel 14 by penis 50, as shown in FIG. 19, channel 14 may assume a substantially circular or ovoid cross-sectional configuration generally conforming to a cross-sectional configuration of an erect penis 50. This transformation of the cross-sectional configuration of collar 12, together with the variations in the functional design variables selected for different portions of the collar 12, may be designed and configured to, by way of nonlimiting example, a) selectively compress the dorsal penile veins, b) grab and support the base of the erect penis in a desired erect state, c) prevent undue compression of the penile nerves, arteries, corpora cavernosa, corpus spongiosus, and urethra, d) controllably bias the erect penis differentially and directionally in the cephalad-caudad plane and/or right-left orientation as desired or needed, e) avoid slippage of the device during sexual activity, f) maintain engorgement and stiffness of the corpora cavernosa posterior to the pubic shield, and any combination of the forgoing.

As used herein, stiffness refers to the resistance of an elastic body to deformation (e.g., extension or elongation) by an applied force. In general, elastic modulus is related to, but not the same as, stiffness. Elastic modulus is a property of the constituent material, whereas stiffness may refer to a property of a structure. That is, the elastic modulus is an intrinsic property of the material; stiffness, on the other hand, may generally refer to a property of the network or architecture of the structure, and may be dependent on the material modulus and the shape and boundary conditions. Because stiffness is a function of the Young's elastic modulus, the material modulus can be used as a comparative measure of the relative stiffness of the collar wall, and a predictor of the deflection upon stretching or expansion of the channel wall.

Strain is a description of deformation in terms of relative displacement of a body. A deformation results from a stress induced by applied forces, in the case here, for example, by the expansion of the penile shaft within the channel 14 upon vacuum activation or other arousal. Because materials of lower stiffness or smaller elastic modulus will deform to a greater degree than the higher elastic modulus materials, the low stiffness materials experience strain or deformation first. As a result, the strain in the material of the higher stiffness or greater elastic modulus is smaller or "limited." As used herein, a wall of the channel 14 that is stiffer, e.g., has a higher elastic modulus, is referred herein as a "strain limiting" wall, e.g., the wall including dorsal ridge 32.

In some embodiments, the prosthesis 10 may be made up of the same material and its elasticity may be engineered by controlling the relative thicknesses of the various regions, so as to obtain regions of higher and lower stiffness. In homogenous elastomers, elasticity may be significantly controlled by tailoring those regions defined by the thinnest walls (e.g., by the structure or region with the lowest resistance to stretching).

Referring again to FIGS. 18 and 19, in some embodiments, the inferior wall of ventral recess 34 may be relatively thin and more compliant in order to prevent compression of the urethra 82 and corpus spongiosum 62 upon expansion of the shaft of the penis 50 within collar 12. Being the most compliant and thinnest, the wall of the ventral recess 34 may be the least resistant to stretching, and the lower perimeter 25 of the collar 12 may become significantly wider than upper perimeter 15 to conform to the underside of the erect penis 50.

With reference to FIGS. 19 and 21, stretching of the collar 12 around the penile shaft reconfigures the walls of the collar 12 to urge dorsal ridge 32 down on the penile veins in the dorsum of the penile shaft thereby inhibiting venous backflow and maintaining the penile erection.

FIGS. 19 and 21 (refer also to FIG. 42) show anatomical cross-sectional views of the shaft of the human penis 50 following expansion of a user's erect penis. The penile shaft is composed of three erectile columns, namely, the two corpora cavernosa 60 and the corpus spongiosum 62, as well as the columns enveloping fascial layers 64, nerves 66, cavernosal arteries 68, superficial dorsal vein (SDV) 70, deep dorsal vein (DDV) 72, dorsal penal arteries 74, and lymphatics (not shown), all covered by areolar tissue 76, and skin 78.

The tunica albuginea 80 becomes thicker ventrally, where it forms a groove to accommodate corpus spongiosum 62. Tunica albuginea 80 of corpus spongiosum 62 is considerably thinner (less than 0.5 mm) than that of corpus cavernosa 60 (approximately 2 mm). The cut surface of corpus cavernosa 60 looks like a sponge. Blood flows to the corpora cavernosa 60 via the paired deep cavernosal arteries 68 of the penis, which run near the center of each corpus cavernosum 60. Corpus spongiosum 62 lies in the ventral groove between the two corpora cavernosum 60. The urethra 82 passes through the corpus spongiosum 62. Corpus spongiosum 62 possesses a much thinner and elastic tunica albuginea to allow for distention of the corpus spongiosum 62 for passage of ejaculate through the urethra 82. The distal extension of the corpus spongiosum 62, the glans penis 84, covers the distal tips of the corpora cavernosa 60 to provide a cushioning effect.

On the dorsal aspect of the corpora cavernosa 60, the superficial and deep dorsal veins 70 and 72, and paired dorsal penal arteries 74, and branches of the dorsal nerves 66 are contained within the deep penile fascia (Buck fascia) 64. This fascia splits to surround the corpus spongiosum 62, and it extends into the perineum into the deep fascia of the ischiocavernosus and bulbospongiosus muscles. The deep penile (Buck) fascia 64 encloses these muscles and each crus of the corpora cavernosa 60 and the bulb of the corpus spongiosum 62, adhering these structures to the pubic and ischial bones and to the urogenital diaphragm.

In some embodiments, collar 12 may be comprised of at least two materials of different hardness and/or elastic modulus, which may provide a resilient but relatively inelastic dorsal ridge 32 as well as relatively elastic and stretchable sidewalls. With particular reference to FIG. 18, in some embodiments ventral wall 42 of ventral recess 34 may be relatively thin and stretchable, forming a protective truss for the user's urethra 82.

Figure 20:
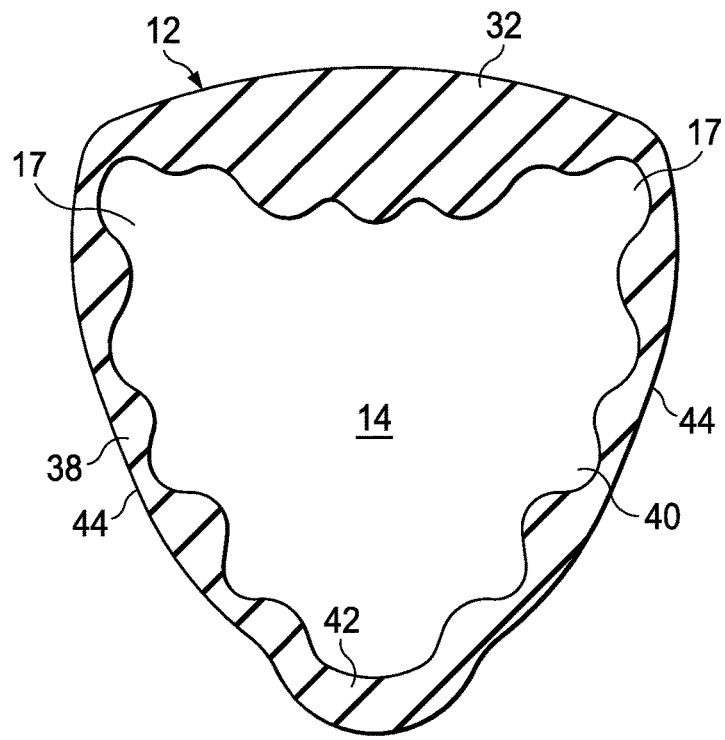
FIG. 20 is a cross-sectional view similar to FIG. 18 showing a ventral recess wall that is relatively thick as compared to the sidewalls.

In some embodiments, as shown in FIGS. 20 and 21, for example, ventral wall 42 may be relatively thick, measuring around 2-4 mm, for example. In some embodiments, the ventral wall 42 may be formed of a relatively higher material hardness. The stiffness of ventral wall 42 may be controlled using a relatively thick ventral wall 42, using a material of relatively higher material hardness, or both. The relatively increased stiffness of ventral wall 42 may provide protection against undue deformation of ventral recess 34 upon expansion of channel 14 by the erect penis 50 and consequent stretching of the sidewalls 44 of collar 12.

Figure 22:
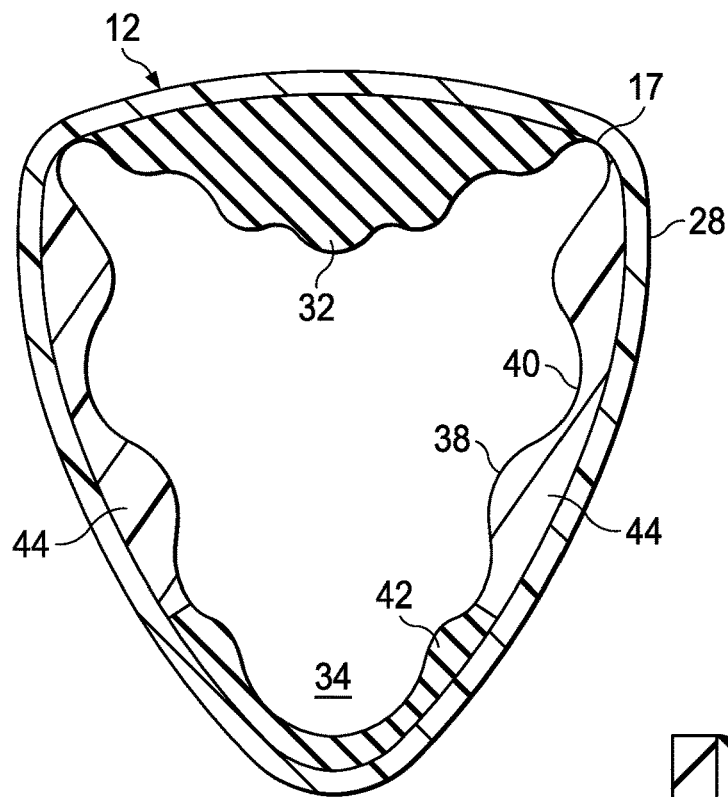
FIG. 22 is a cross-sectional view of a penile prosthesis collar embodiment depicting collar segments formed of different polymer materials. In an alternative embodiment, the segments are formed of the same material, but having different hardness or elastic modulus.

In some embodiments, as shown in FIG. 22, a segment of relatively greater hardness may be embedded in ventral wall 42 around the ventral recess 34 to form a strain-limiting layer that further protects the urethra 82 and corpus spongiosum 62 from compression by ventral wall 42 upon expansion of channel 14 by an erect penis 50. The molded section 42 can be secured to the softer and more elastic sidewalls using conventional molding methods, such as insert molding, for example.

In some embodiments, sections of the same or similar materials can be adhered using a small molecular silicone precursor e.g., an adhesive. First, a small molecular silicone precursor can be layered onto a first layer of material. Then, a second layer of material can be placed on top of the first layer of material with the silicone precursor. The composite material is then placed into an oven to cure and bond the layers. Of course, any suitable method of manufacture may be used.

With reference to the particular embodiment illustrated in FIG. 22, it may be advantageous to form sidewall 44 segments of a silicone elastomer with a hardness as measured on a durometer scale of, for example, Shore A10; dorsal ridge 32 with a hardness of Shore A20; the ventral wall segment 42 with a hardness of Shore A15. Of course, other hardness values may be used. Expansion of channel 14, in this particular example, would further thin the sidewall grooves 40 and flatten the sidewall ribs 38, as the sidewalls 44 elongate differentially, whereas dorsal ridge 32 and ventral wall 42 would elongate to a lesser degree. At the same time, the volume of channel 14 would increase. To accommodate the differential elongation of two adjacent or opposing walls of channel 14, the structure surrounding the expanding volume bends outward as demonstrated in FIGS. 19 and 21. Circumferential expansion may be symmetrical or asymmetrical depending on the relative thickness and/or material modulus of the various wall segments. Upon pressurized expansion, channel 14 spanning the length of collar 12 may be configured to controllably bend and assume various configurations along the longitudinal axis of channel 14.

In some embodiments, a sidewall of collar 12 may be configured to stretch upon expansion of the user's penile shaft within channel 14. A sidewall that is configured to stretch upon expansion, also called an actuating wall, may, for example, have an average thickness less than about 2 mm. In contrast, a wall that is configured not to expand upon pressurization, also called a strain limiting wall, may have a thickness greater than about 2 mm. The size of the strain limiting wall may also depend on the relative stiffness compared to the actuating wall. For example, if the elastic modulus of the strain limiting wall is substantially greater than that of the actuating wall, then the strain limiting wall can be substantially smaller.

Figure 23:
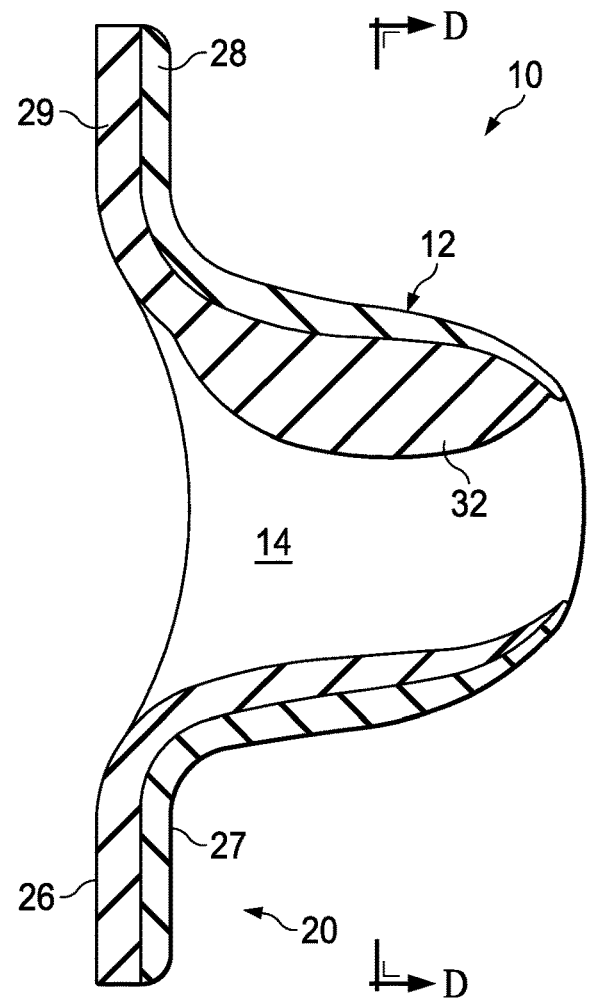
FIG. 23 is a cross-sectional view taken along a mid-longitudinal plane of a penile prosthesis wherein the flange portion is formed of forward facing and rearward facing layers, wherein the forward facing layer extends anteriorly to form the outer layer of the collar, and the rearward facing layer extends anteriorly to form the inner layer of the collar, including the dorsal ridge.
Figure 24:
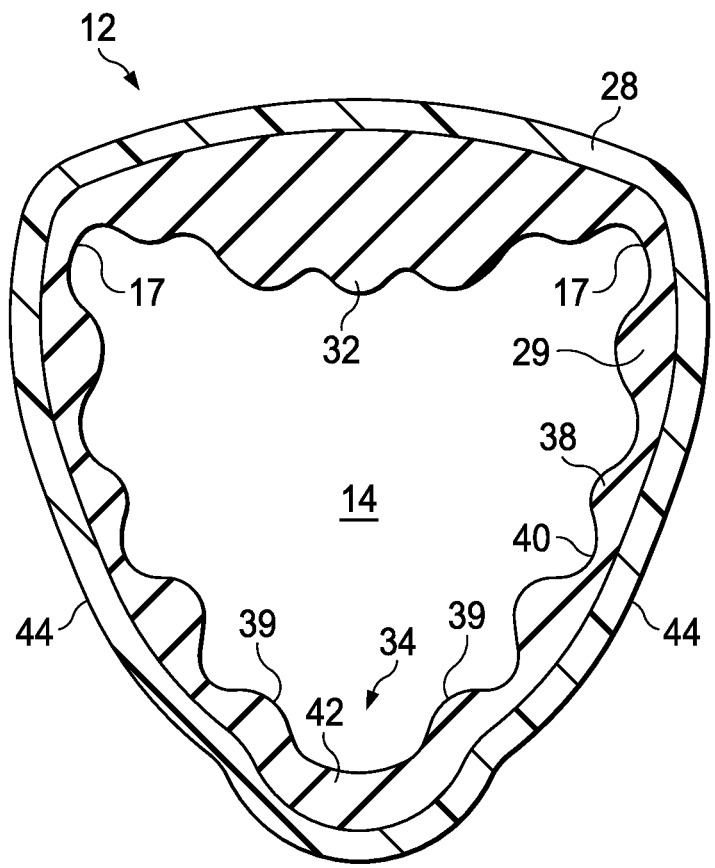
FIG. 24 is a cross-sectional view of the collar of FIG. 23 taken along the line D-D shown in FIG. 23.

In some embodiments, penile prosthesis 10 may be formed of two or more contiguous layers. For example, as shown in FIGS. 23 and 24, penile prosthesis 10 may include an outer layer 28 and an inner layer 29. In some embodiments, outer layer 28 may include a material of a lower modulus of elasticity and/or lower hardness than that of a material forming inner layer 29, so that during expansion of channel 14, the elasticity of prosthesis 10 is primarily controlled by the elasticity of inner layer 29. Outer layer 28 may be more elastic and softer, thereby presenting a relatively more agreeable interface to the sexual partner's tissues. Dorsal ridge 32 may be integrally formed with the inner layer 29 and may be relatively firm.

Figure 32:
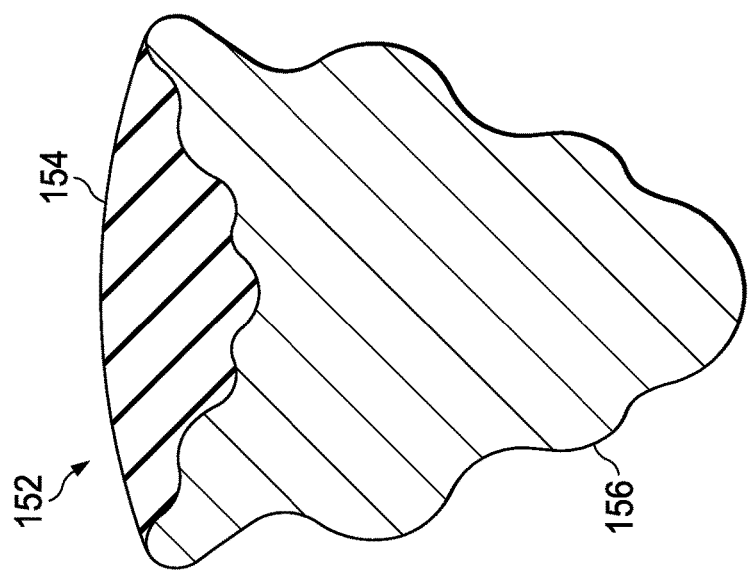
FIG. 32 is an elevational cross-sectional view of a mold core constructed in accordance with an embodiment of the present invention shown as a subassembly by itself apart from the outer mold halves.
Figure 35:
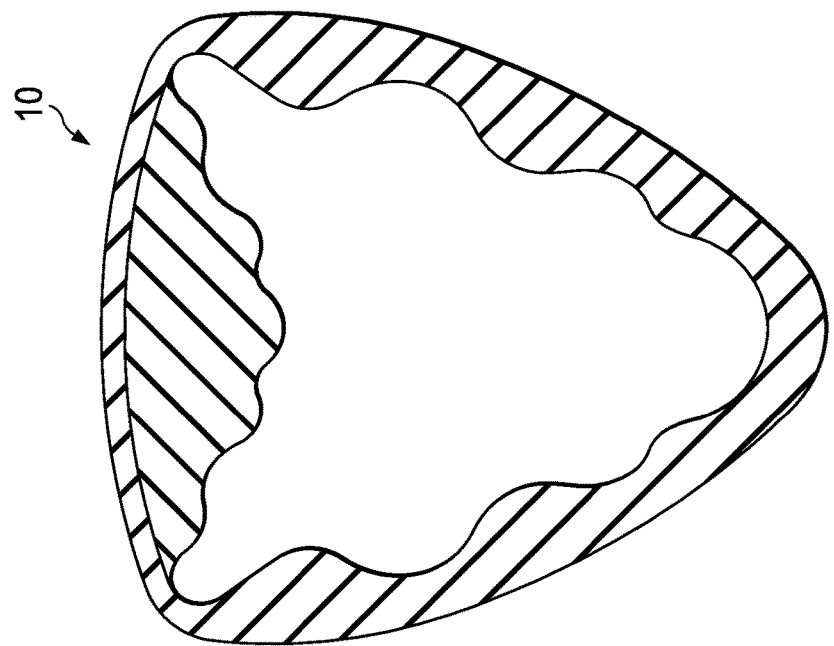
FIG. 35 is a cross-sectional view of a penile prosthesis embodiment formed in the mold assembly depicted in FIGS. 32-34.
Figure 34:
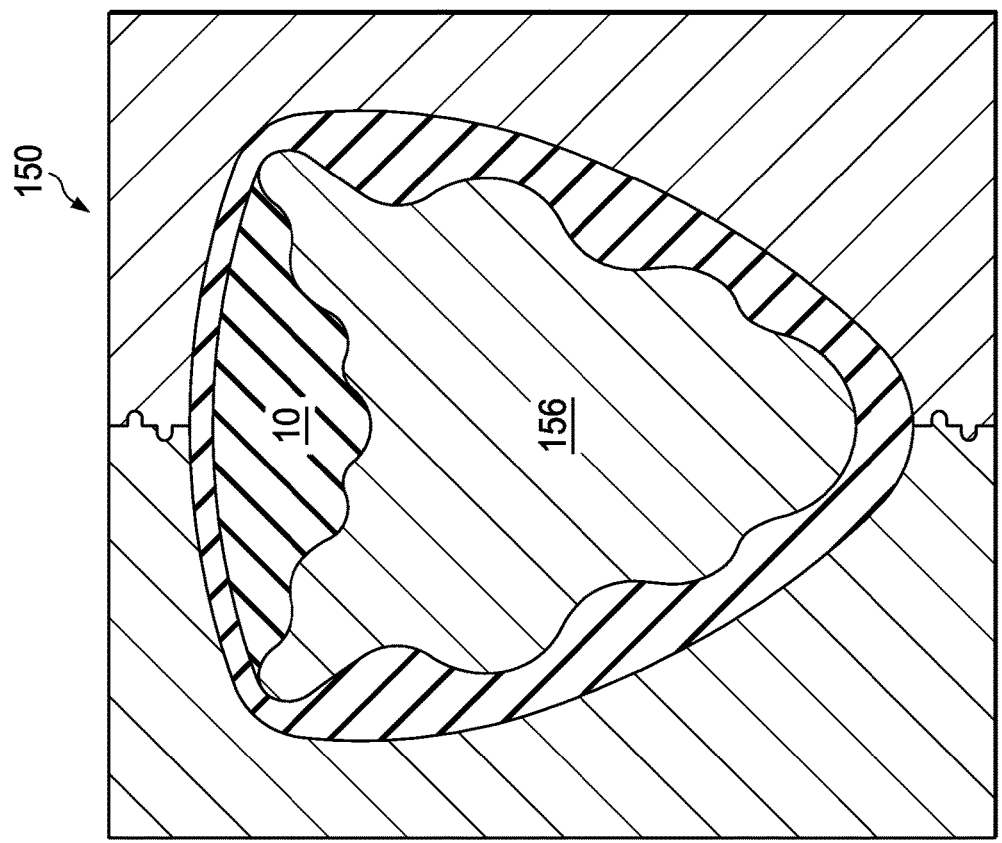
FIG. 34 is an elevational cross-sectional view of the main components of the mold assembly of FIG. 33 arranged according to some embodiments. Note the dorsal ridge insert positioned in the corresponding concavity of the mold core. The rest of the space of the collar within the mold cavity has been filled with liquid polymer by an injection molding process.

FIG. 24 is a cross-sectional view taken along the line D-D of FIG. 23 depicting features of some embodiments of the midportion of collar 12. For example, dorsal ridge 32 may be molded separately, such as by injection molding. The molded part may be inserted into a corresponding cavity of an inner mold or mandrel that is designed and configured to assume the shape and dimension of pubic shield 20 and channel 14 of collar 12, see FIG. 32, followed by sequential dip molding or layering of liquid polymer that forms inner layer 29, followed by layering of outer layer 28. The composite layers are then cured and removed from the mandrel. In some embodiments, a silicone elastomer may be used in compositions for making one or more of dorsal ridge 32, outer layer 28, and inner layer 29. If such compositions are used, the portions 28, 29, 32 may generally bond together well upon curing.

Variations on this technique are possible and can be readily altered based on the teachings herein to suit many applications. For example, as shown in FIG. 22, one could use three or more polymer compositions (e.g., one for ventral wall 42, one for dorsal ridge 32, and one for sidewalls 44), each with different moduli of elasticity, so long as at least the outer layer 28 is of lower modulus and the dorsal ridge 32 is of a higher modulus.

Although some of the figures illustrate the combination of only two portions of different moduli of elasticity and/or hardness, some embodiments of the invention may include more than two portions, where the material forming the portions could each have a different modulus.

In some embodiments, a wall of collar 12 may be configured to elongate or bend upon expansion of channel 14, also called an actuating wall, which can have a thickness less than 3 mm, for example. In contrast, a wall that is configured not to elongate or bend upon expansion can have a thickness greater than 3 mm, for example. The size or configuration of dorsal ridge 32 (strain limiting) contributes to its relative stiffness compared to the sidewalls 44 (actuating wall). Of course, any suitable materials, elastic modulus, and thickness combinations may be used, depending on the desired properties and characteristics of the prosthesis 10.

In some embodiments, a choice of materials (e.g., silicone of different hardness) coupled with the design of the wall segments of collar 12 may help determine the response of the device to expansion. Generally, the expansion force necessary to achieve a particular amplitude of actuation scales with the stiffness of the wall segments. Different combinations may provide a different behavior with stretching or bending, upon expansion of collar 12. For the same channel geometry, the bending may increase with increasing difference in elastic modulus between the actuating wall and the strain limiting wall.

FIG. 18 illustrates sidewalls 44 having multiple lateral wall ribs 38 and lateral wall grooves 40 protruding into channel 14. The inner folds facilitate the stretching and recoil of the sidewalls 44 upon expansion and contraction of channel 14. Corrugations or pleating prescribe the circumferential expanded configuration of the device around the erect penile shaft as demonstrated in FIGS. 19 and 21. As channel 14 expands circumferentially, dorsal lateral recesses 17 widen substantially, and dorsal ridge 32, acting as a strain limiting wall, becomes biased inwardly into channel 14. As shown in FIGS. 19 and 21, dorsal ridge 32 may bear down on the dorsal region of penis 50 to restrict blood flow through dorsal veins 70 and 72.

With reference to FIG. 23 and FIG. 24, in some embodiments, the pubic shield 20 and the collar 12 of penile prosthesis 10 may comprise at least two polymeric materials of different elastic modulus, which allows for a flexible but relatively non-distensible shield 20 and an appropriately stretchable and relatively softer collar 12. The forwardly facing outer surface 27 of the pubic shield 20 may be formed of a compressible and relatively softer elastic material (e.g., a hardness on the durometer scale of about 10) than the rearward facing inner surface 26, which may be formed of a harder material (e.g., a hardness on the durometer scale of about 20) that gives the flange 20 structural integrity and cross-sectional stability, and prevents buckling of the flange 20 into the vacuum cylinder. The collar 12 is preferably integrally formed with the shield 20, and may be formed in a two-piece construction that includes a dorsal ridge 32 which has essentially the same hardness as the inner layer 29 which forms the inner wall of collar 12.

In some embodiments, with reference to FIG. 24, segments forming a penile prosthesis 10 may be prepared by casting them individually in a suitable injection mold, dip casting, or other suitable molding technique. FIG. 24 is a cross-sectional view taken along the line D-D of collar 12 of the penile prosthesis 10 shown in FIG. 23. One feature of external penile prosthesis 10 is the configuration of channel 14 in the relaxed unstretched configuration, shown in FIG. 24, for example, and its deformation by an expanding penile shaft therein, shown for example in FIGS. 19 and 21. Collar 12 surrounds channel 14, which is illustrated as being generally triangular but it could be trefoil or some other near-triangular configuration. A prominent dorsal ridge 32 projects from the upper wall of collar 12 into channel 14, forming one side of the triangle.

In some embodiments, channel 14 may be approximately triangular in shape. For example, as shown in FIG. 22 and FIG. 24, diametrically opposite of dorsal ridge 32 is a ventral recess 34. The ventral recess 34 may form the inner angle of an approximately triangular channel 14. A pair of dorsolateral recesses 17 diametrically opposite the sidewalls 44 may help define the other two angles of the triangle.

By way of example, and not limitation, the maximum thickness of the dorsal ridge 32 may be about 12 mm (0.47 inch), its side-to-side width may be about 16 mm (0.63 inch), and its longitudinal dimension or length may be about 23 mm (0.9 inch). The distance between dorsal ridge 32 and ventral wall 42 across channel 14 may be about 18 mm (0.71 inch). The distance between inferolateral ribs 39 across ventral recess 34 may be about 11.6 mm (0.45 inch) when channel 14 is not stretched. The dimensions prescribed may be approximate and depend on the penis size of the individual.

As shown in FIG. 24, a pair of inferolateral ribs 39 project from the inside of the lateral walls 44 into ventral recess 34 of channel 14. In FIG. 24, the channel 14 is shown presently unstretched so the ventral recess 34 is at a narrower width than it may be when stretched.

In some embodiments, penile prosthesis 10 may be designed to be installed around the base of the penile shaft with the male organ still in a flaccid state and utilizing a vacuum erection device. However, males who are able to have an erection may choose to put on the device using only a lubricant, avoiding the use of a vacuum device.

Figure 25:
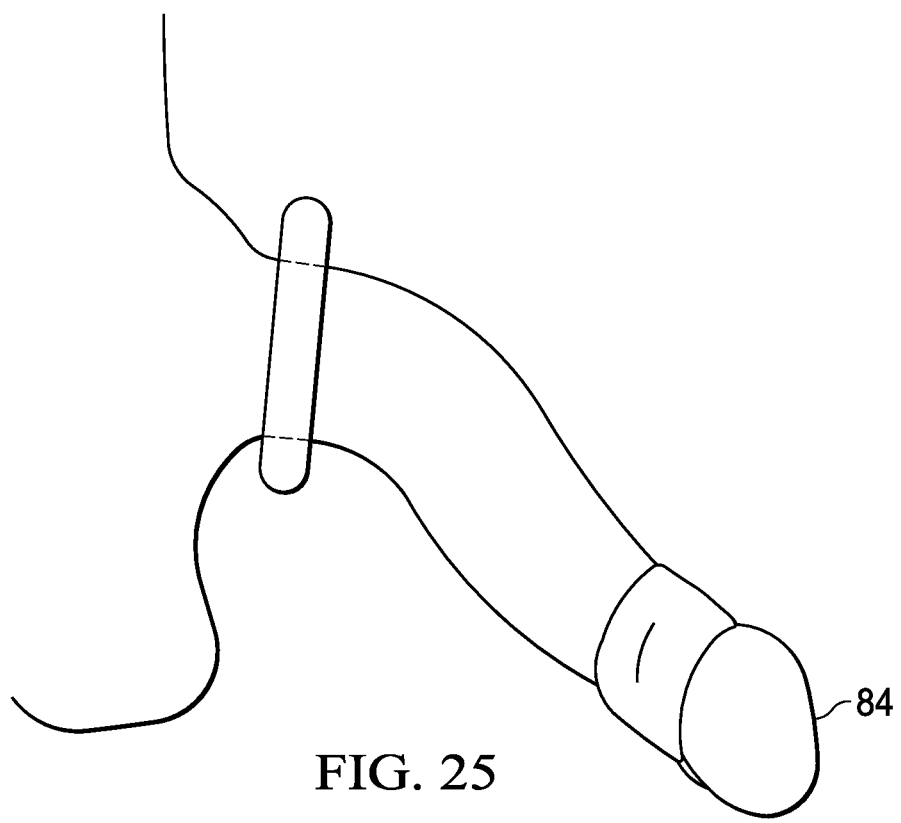
FIG. 25 is a side view of a conventional prior art constrictor device mounted on the base of a penis, depicting circumferential constriction of the penile shaft, whereby the base of the penis behind the constriction remains flaccid and the penile shaft is disposed to dangle downwards.

FIG. 25 illustrates a prior art constricting band or ring applied at the base of a user's penis. Devices of this kind have been used alone (if the patient is able to achieve erection) or in combination with conventional commercially available vacuum erection devices that allow the user to transfer the constricting ring from around the constricting device to the base of his penis. Use of bands or rings with a vacuum erection device requires that either one ring or several bands, doubled or redoubled, be slipped over the open end of the plastic cylinder. Once erection is achieved, the constriction ring or band is slipped off the open end of the cylinder, whereupon it contracts around the base of the erect penis. Placement of the ring or band around the erect penis significantly restricts the flow of blood back out of the penis. However, the pinch-off encompasses veins, arteries, nerves, the corpora cavernosa, the corpus spongiosus, and the urethra. Shortly after the pinch-off, therefore, the penis turns blue and numb, and the circumference where the ring is pinching starts to hurt. The part of the penis behind the pinch-off at the penis root remains limp, so that the stiff portion of the penis before the pinch-off dangles down instead of being erect. Sexual activity with a partner is often cumbersome. If orgasm is reached, the ejaculate cannot escape through the choked off urethra, but is emptied backwards into the bladder.

Figure 26:
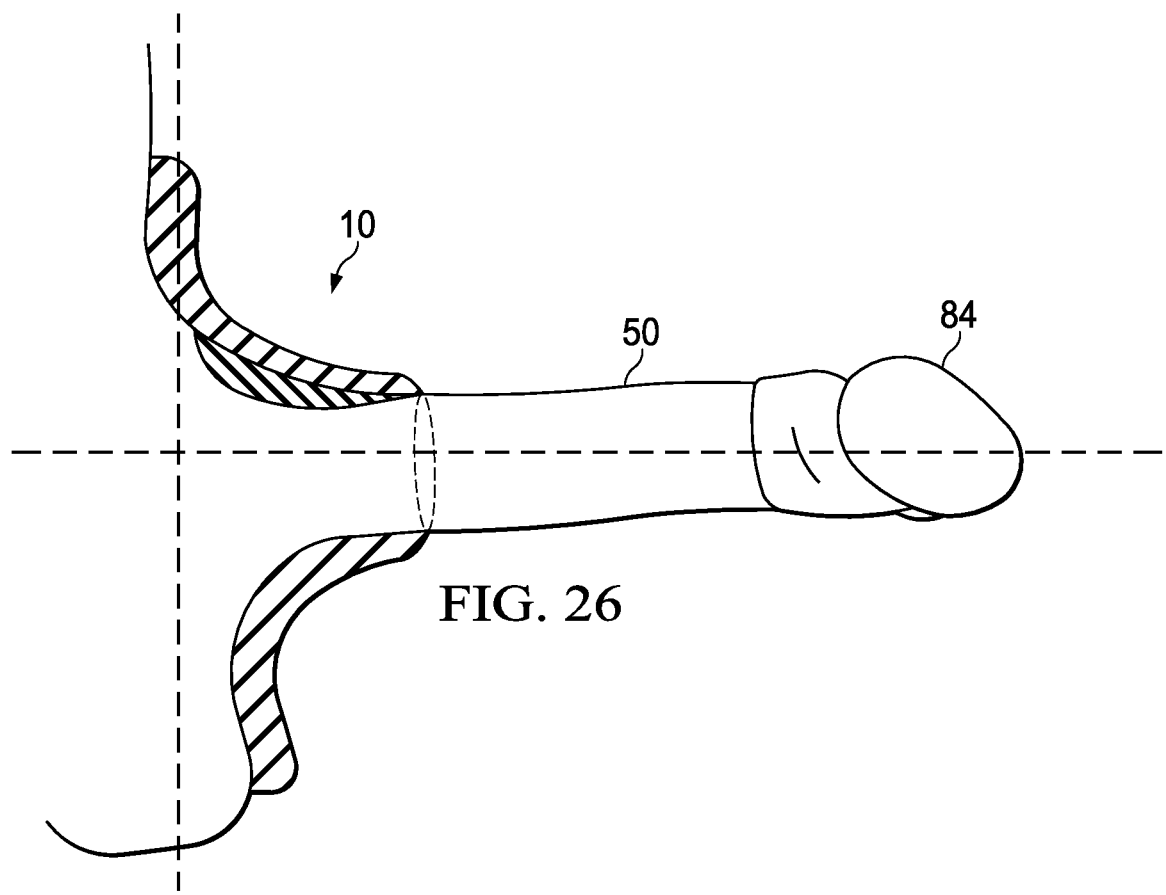
FIG. 26 is a side view of a penile prosthesis depicting an embodiment of the present invention mounted on the base of a penis, showing selective compression of the dorsal veins by the dorsal ridge and support of the penile base by the prosthesis, whereby the penile shaft assumes a normal straight erect posture.

FIG. 26 shows an exemplary embodiment of a penile prosthesis 10 of the present invention surrounding the base of a user's penis 50 in the usual erect posture. The penile prosthesis 10 may be placed in position with the aid of a lubricant with or without the use of a conventional vacuum device as described herein.

Figure 27:
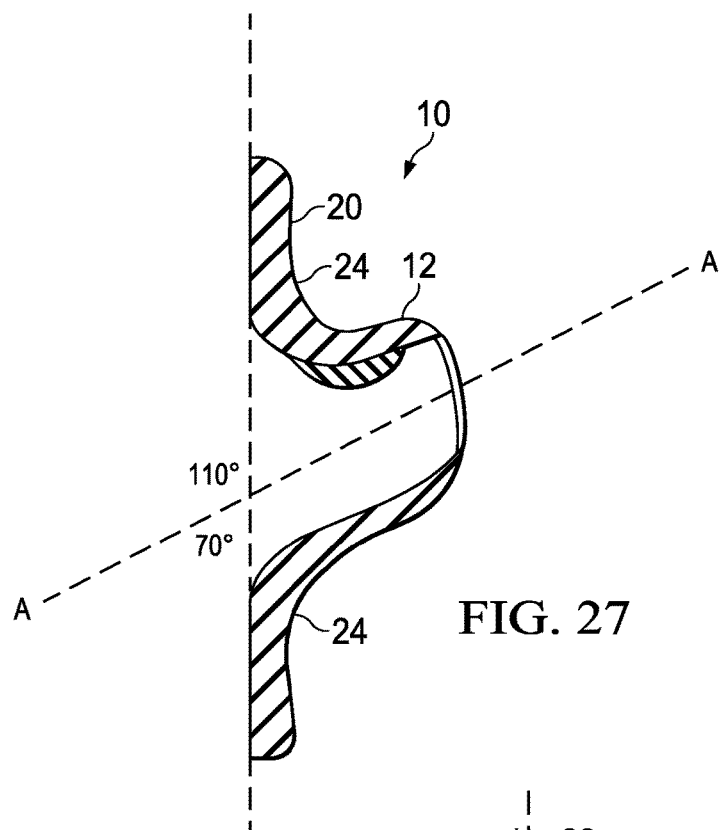
FIG. 27 is a cross-sectional view of a penile prosthesis taken along a mid-longitudinal plane depicting an embodiment whereby the longitudinal axis of the collar is biased cephalad with respect to the plane of the annular flange.
Figure 28:
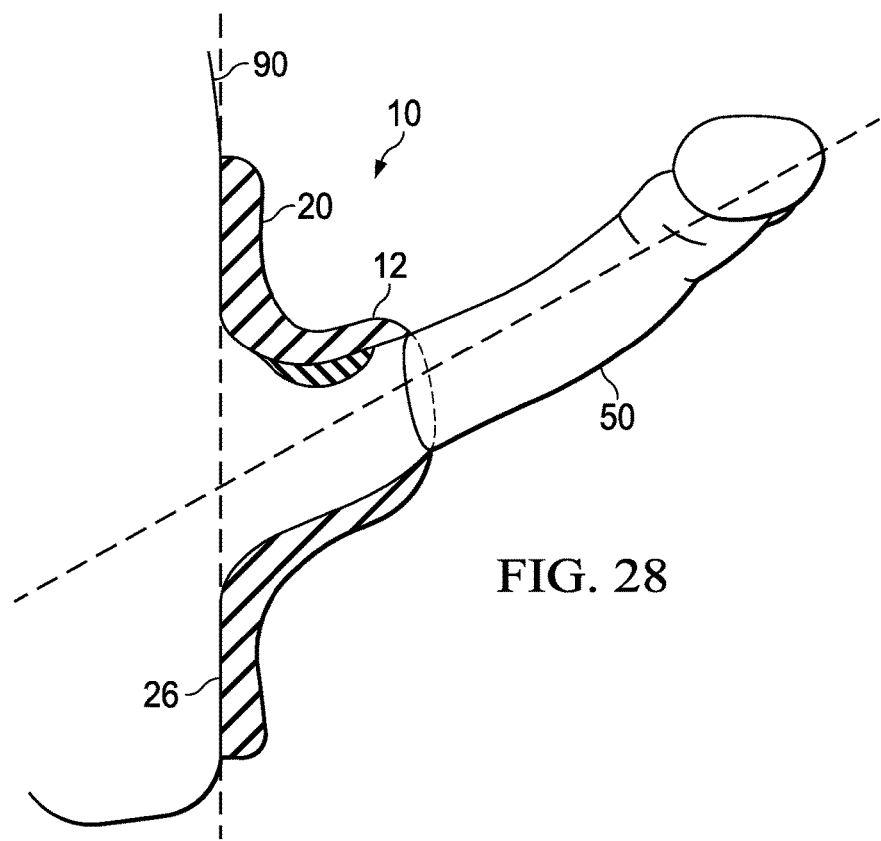
FIG. 28 is a cross-sectional view showing the penile prosthesis of FIG. 27 mounted on the base of a user's penis, wherein the prosthesis stabilizes the erect penis and orients it in a favorable upward direction.

Referring now to FIGS. 27 and 28, in some embodiments, the central axis A-A of collar 12, as viewed in the sagittal plane of penile prosthesis 10, may be oriented in a caudal-cranial direction. As shown in FIGS. 27 and 28, when penile prosthesis 10 is placed over the user's erect penis 50 so that collar 12 encircles the shaft of penis 50, and a rearward facing inner surface 26 of pubic shield 20 rests flush against the user's groin 90, collar 12 biases the shaft of the penis 50 upward into a preferred functional angulation. Further, this improved penile angulation holds prosthesis 10 firmly in a posteriorly retracted position and prevents the prosthesis 10 from sliding forward over penis 50. Another advantage of this improved angulation is enhanced compression of the dorsal penile veins by dorsal ridge 32, while diminishing the degree of further urethral compression.

Figure 29:
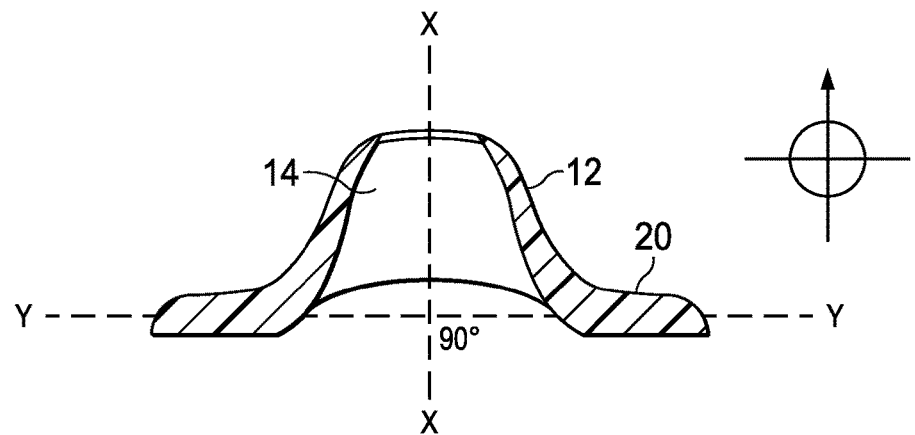
FIG. 29 is a cross-sectional view taken along a mid-longitudinal plane of a penile prosthesis embodiment wherein a central axis of the frustoconical collar is oriented substantially perpendicular to the annular flange.

Referring to FIG. 29, in some embodiments, a centrally disposed frustoconical collar 12 may enclose a channel 14 having a central axis X-X that forms a 90-degree angle with the axis Y-Y of pubic shield 20. When the device shown in FIG. 29 is positioned over the user's penis, the penis will point substantially in a straight orientation with respect to the longitudinal axis X-X.

Figure 30:
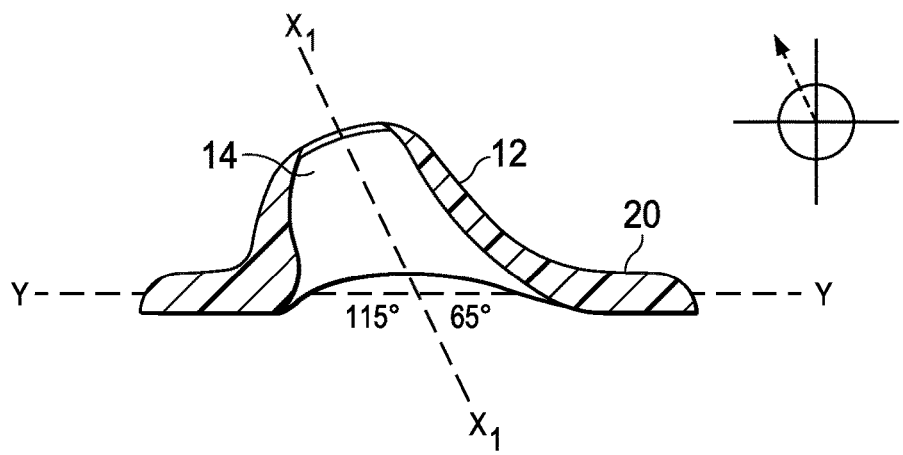
FIG. 30 is a cross-sectional view taken along a mid-longitudinal plane of a penile prosthesis embodiment wherein a central axis of the frustoconical collar is angled to the left with respect to the annular flange.

In other embodiments shown in FIG. 30, central axis $X_1$-$X_1$ of channel 14 may be biased to the user's left, forming an angle of, for example, 115 degrees to the user's left and 65 degrees to his right. Accordingly, this particular configuration of collar 12 will deviate the user's penis towards his left.

Figure 31:
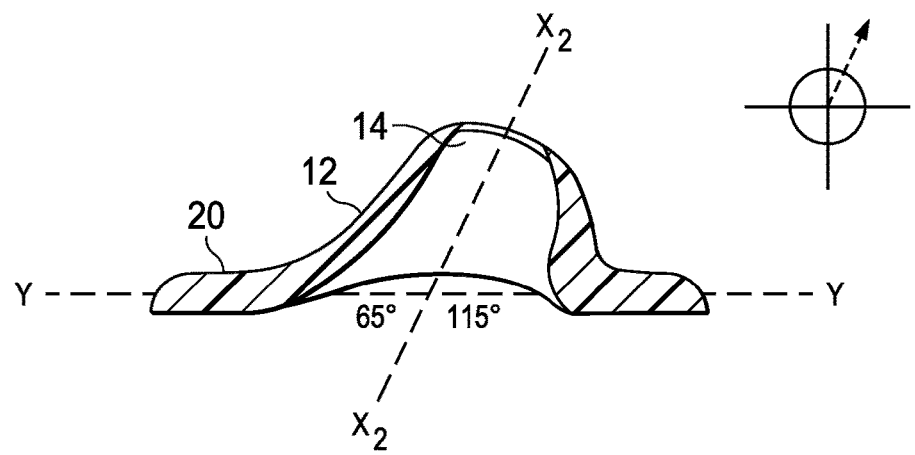
FIG. 31 is a cross-sectional view taken along a mid-longitudinal plane of a penile prosthesis embodiment wherein a central axis of the frustoconical collar is angled to the right with respect to the annular flange.
Figure 33:
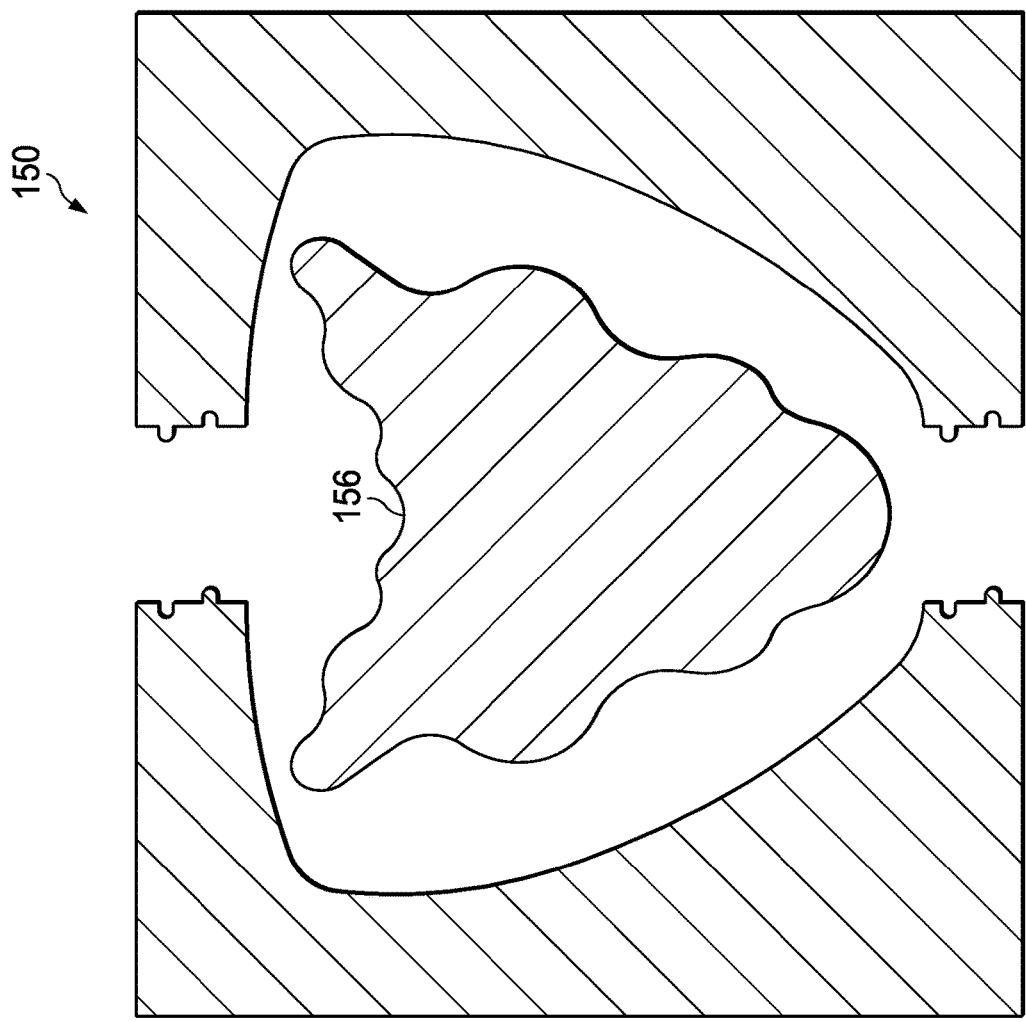
FIG. 33 is an exploded cross-sectional view of the mold halves and associated mold core component of a mold nest assembly.

In yet another embodiment, shown in FIG. 31, this particular orientation of collar 12 along axis $X_2$-$X_2$ would deviate the user's penis to his right. Of course, such angulation may be variable, and formation of penile prostheses having a range of angulations are feasible.

In certain embodiments of the present invention, a penile prosthesis having a collar 12 that is configured to form a predetermined angle with respect to the plane of the annular flange 20 may be used for the treatment of selected patients suffering from Peyronie's disease. Peyronie's disease is manifested by an abnormal bend that occurs in the erect penis of the sufferer and can be associated with painful erection and/or painful intercourse. Peyronie's disease is related to the development of scar tissue or plaque that forms on tissues (e.g. tunica albuginea) inside the penile shaft. One non-surgical approach for the treatment of Peyronie's disease includes injecting drugs into the plaques that lessens the compression applied by the plaque to the erect penis, however the efficacy of this approach is limited. Surgical treatment for Peyronie's disease includes excising portions of the tunica albuginea and corporal plication.

In some embodiments, the angle formed between the collar 12 and the pubic shield 20 may be configured to change upon expansion of the penile shaft within the device upon pneumatic actuation of the vacuum device in such a manner that a force is exerted on the penis to bend it in a certain predetermined direction. For example, the penile prosthesis device may be configured to deflect the penile shaft to correct deformity in a stent-like fashion after repeated use over time.

Certain types of penile deformity may be correctable or improved during sexual intercourse. Further, such deformity may be corrected over a period of time following repeated use of the device by the user alone or with a partner. Unlike traditional hard splints or stents used in other parts of the body such as in dentistry or orthopedics, a specially designed penile prosthesis intended to correct a particular penile deformity may act as a soft actuator which maintains its adaptive properties when it is provided with a particular form or collar-flange angle, or when it is pressurized or vacuum actuated such that it can partially conform to the shape of the erect penile shaft. Furthermore, the amount of deflective force applied on the erect penis can be spread out over a large surface area in a controlled manner because the elastomeric material used can easily deform. In this way, a corrective penile prosthesis design for treatment of a specific deformity can effectively provide momentary or permanent benefit without injuring the body organ.

In some embodiments, an external penile prosthesis may be in the form of an actuator that may be created, for example, by molding one or more pieces of elastomeric material into a desired shape. Such an actuator may include a collar portion having a hollow interior or channel that can be extended or expanded with the user's penis in the state of erection to pressurize, inflate, and/or actuate the actuator as further described in U.S. patent application Ser. No. 15/895,299, filed Feb. 13, 2018, titled "External Penile Erection System," which is incorporated herein by reference. Upon actuation, the shape or profile of the actuator changes. In certain cases, actuation may cause the actuator to curve or straighten into a predetermined target shape. One or more intermediate target shapes between a fully unactuated shape and a fully actuated shape may be achieved by partially expanding the actuator. The actuator may be actuated using a conventional or modified erection vacuum device thereby changing the degree to which the collar portion of the actuator bends, twists, and/or extends.

In some embodiments, all of the elements of the prosthesis may be fabricated from a moldable, pliable, elastomeric material such as silicone rubber because of its inert, non-wetting surface, durability, and other desirable characteristics. Other materials that are commercially available or yet to be developed may also be used.

The collar 12 and shield 20 portions may be formed in a mold having a mold cavity of corresponding shape. The collar 12 portion of the mold cavity may be loaded with a silicone rubber material which, when cured, may be relatively soft and elastic while the shield 20 portion of the mold cavity may be loaded with a silicone rubber material which, when cured, may be of greater stiffness. The silicone rubber materials for the collar 12 and shield 20 may be compatible with each other and may display the same or similar desirable properties except that the collar 12 portion may be substantially more elastic than the shield 20 portion. For example, the collar 12 material described may have a modulus of elasticity whereby it may be stretched up to three or five times its original dimensions while maintaining adequate tear strength. Additionally, collar 12 may provide a softer feel to both partners, which is a very desirable feature. In contrast, shield 20 may be made from a silicone rubber compound which may be approximately half as elastic, and may be capable of being stretched approximately two or three times its original dimensions. Desirably, shield 20 presents a relatively firm wall against the entry portion of a vacuum tube.

In some embodiments, the prosthesis 10 may be comprised of at least two polymeric materials of different elastic modulus, which allows for a flexible but relatively non-distensible shield portion as well as a collar with elastic and stretchable collar portions. The regions of differing durometer/elasticity in the device can be fabricated and achieved in a variety of ways. In exemplary embodiments, the regions may be formed in an edge-to-edge manner or along an overlapping border region using conventional overmolding, insert molding, and/or dip molding techniques, for example. It will be appreciated that the prosthesis could also be formed by layering materials of differing elasticities, providing layers having different thicknesses, providing reinforcement fibers or materials which create regions of different durometer within a matrix of the same material; in other exemplary embodiments, inflatable members may be interposed between the layers or regions of the structure which may be controlled by the user in the manner of a soft robotic.

In general, some embodiments of the present invention may provide an external penile prosthesis 10 having elements with different thicknesses and different material moduli, which upon stretching around a penile shaft, support the shaft in an erect state and/or control its deflection. In some embodiments, such penile erection augmentation may depend at least partly, however, on having an expandable collar 12 wall chosen to accommodate the size and rigidity of a particular penis being treated, as penile states of erection and rigidity even in the same individual may vary from time to time, and the same user may prefer a device that provides a different degree of constriction. Multiple components of differing hardness may be combined into the same device collar such that one part of the wall is less distensible and another part of the wall is more compliant or elastomeric, such that when the device is applied to a user's penis, both the non-distensible and compliant components are activated simultaneously.

With reference to FIGS. 32-35, in some embodiments of a method of manufacture of a penile prosthesis, a two-piece mold 150 may be used to form the lateral wall ribs and lateral wall grooves of the sidewalls. An outer mold may define the outer contours of the two-piece mold, and the mold cavity can be filled with one or more liquid polymer parisons to form the sidewalls. Once set, the two-piece mold can be separated and the parts removed. The other segments may be molded in a similar fashion. For example, a mold core 152 may include a dorsal ridge mold core 154 and a central channel mold core 156. Central channel mold core 156 may be placed within mold 150, and polymeric materials may be injected therein to form prosthesis 10. The penile prosthesis 10 may then be assembled from the preformed segments by placing the segments into a master mold. For example, the segments may be bonded together using a heat fusing process.

Figure 36:
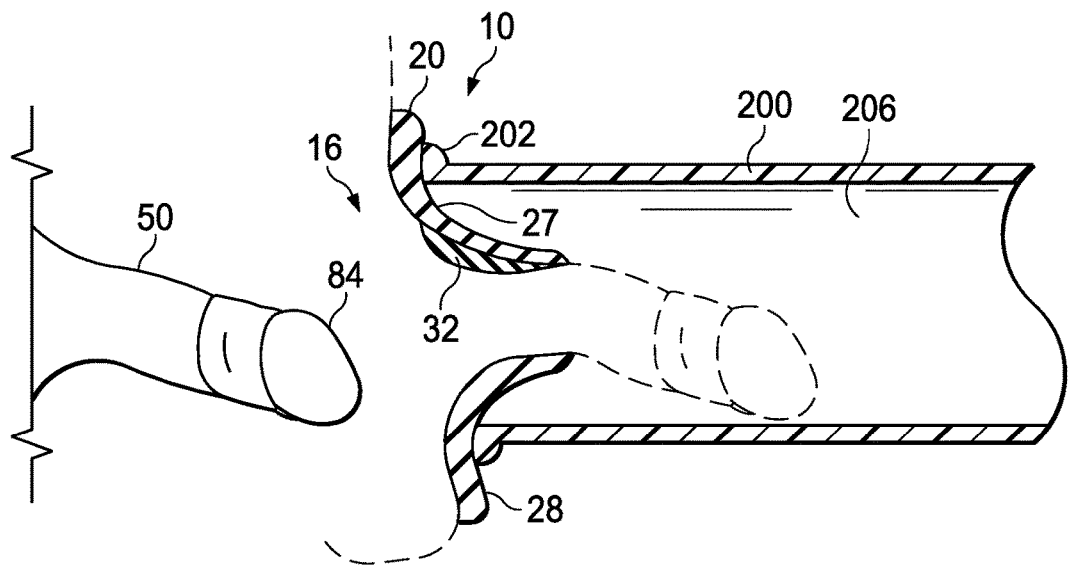
FIG. 36 is a schematic side elevation view depicting a penile prosthesis positioned against the front end opening of an evacuation cylinder, with the user's flaccid penis before and after (dotted lines) initial activation of the vacuum chamber.

FIG. 36 illustrates an embodiment for how a penile prosthesis 10 may serve as an erection obtaining and maintaining device in conjunction with a conventional vacuum tube 200 for receiving the user's penis 50. In some embodiments, it is not necessary to use a separate diaphragm (not shown) for sealing the open end 202 of the vacuum tube 200 around the penis. Instead, penile prosthesis 10 may be placed directly over the open end 202 of vacuum tube 200 whereby an airtight seal is obtained between the soft and smooth front outer surface 27 of pubic shield 20 and open end 202 of vacuum tube 200.

Referring to FIG. 36, penile prosthesis 10 may be positioned upon the front opening of conventional vacuum tube 200, and the user's flaccid penis 50 is shown approaching the funnel-like proximal opening 16 of pubic shield 20. The forwardly facing outer surface 27 of shield 20 rests flush against the front edge 202 of vacuum tube 200 creating an air-tight seal. As the glans penis 84 rests snugly within the funnel-like opening of prosthesis 10 and the vacuum apparatus is activated, the vacuum within the chamber 206 automatically draws penis 50 (dotted line) into the chamber. Pubic shield 20 is sufficiently firm and extends radially a sufficient distance beyond the circumference of the open end of vacuum tube 200 so that it is not pulled into the chamber 206 during the evacuation cycle.

Figure 37:
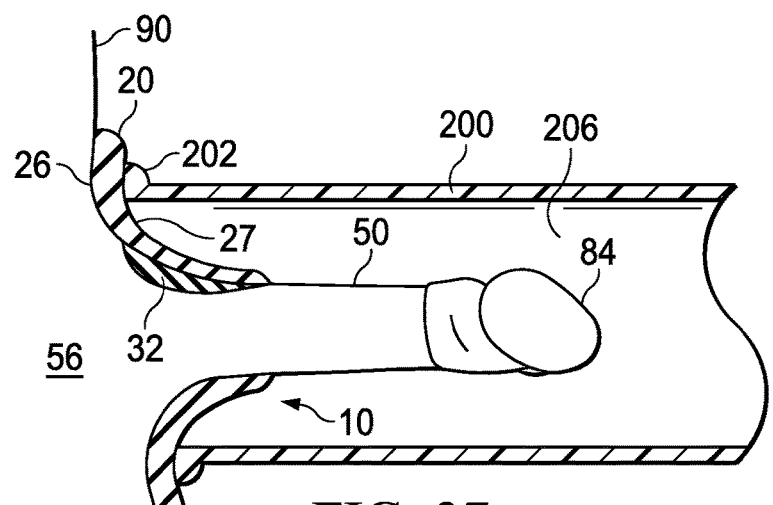
FIG. 37 is a schematic side elevation view similar to FIG. 36 following the flaccid penis being slipped into the evacuation chamber and following vacuum activation; note the air-tight seal being formed between the annular flange of the penile prosthesis and the circumferential edge of the vacuum device along the forward facing sealing surface of the flange, and with the user's groin along the rearward facing surface of the flange; the penis is semi-erect at this stage.

FIG. 37 illustrates the penile prosthesis 10 after it has been deposited on the flaccid penis 50 (dotted line). At this time, the dorsal ridge 32 of collar 12 is bearing down on the top of the penis 50 at its base snugly and not loosely if the appropriate channel 14 size has been selected. The user may now perform pelvic muscle contraction exercises to force blood under pressure into his penis to augment the action of the vacuum tube to produce a firmer erection. The root 56 of the penis behind the prosthesis 10 also becomes rigidized with the rest of the penis when an erection has been obtained. The sidewalls of collar 12 bear inward on the now rigidized corpora cavernosa, thus supporting the penile shaft together with surrounding collar 12 against shield 20, which rests against the user's groin 90.

Figure 38:
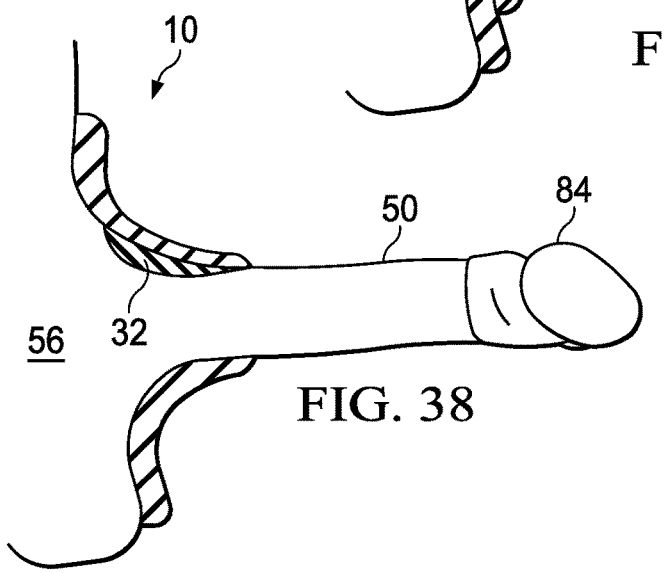
FIG. 38 is a schematic side elevation view of a fully erect penis with the penile prosthesis applied at its base, following removal from the vacuum chamber.
Figure 41:
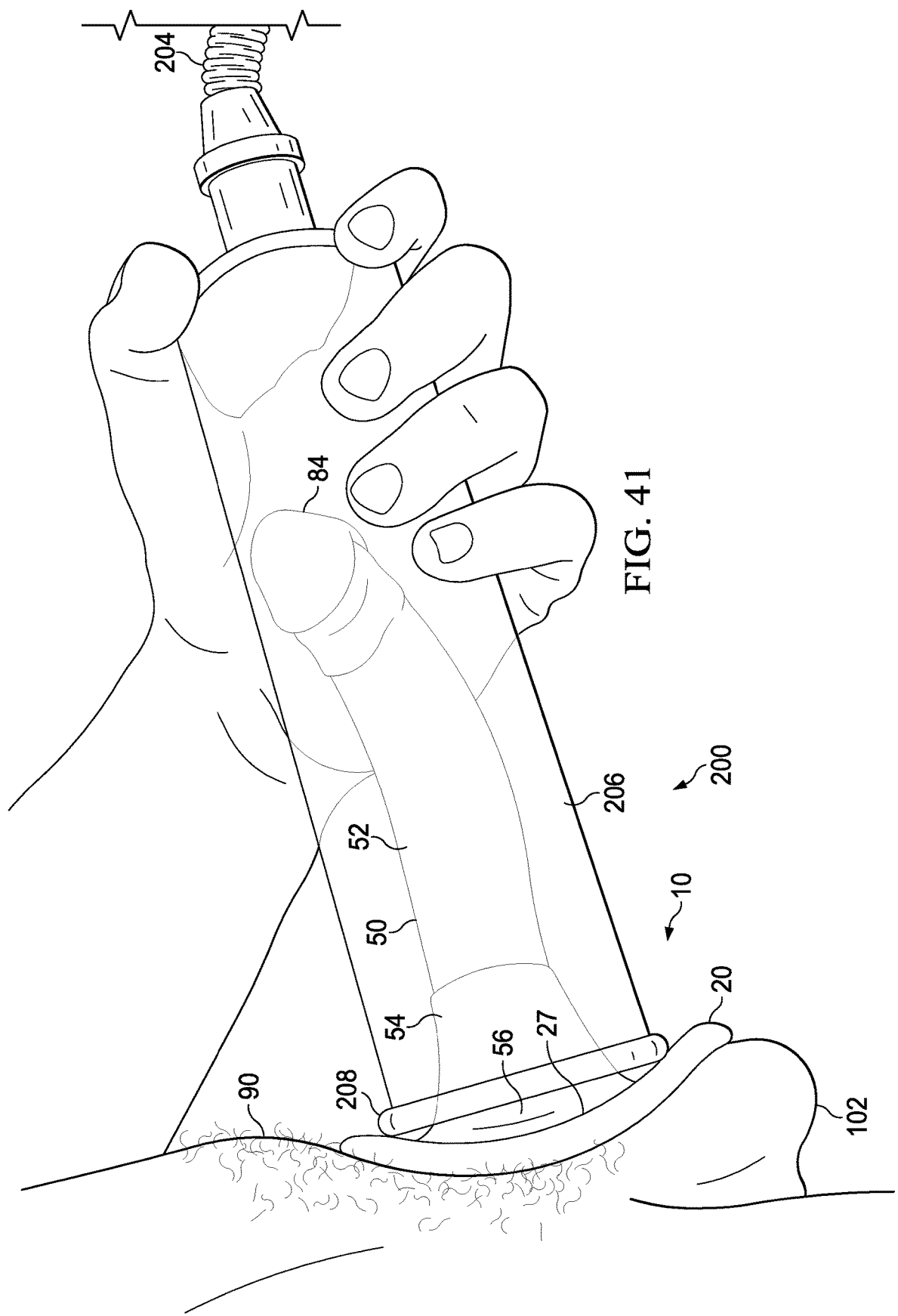
FIG. 41 is a side elevation view depicting a penile prosthesis positioned around the base of an erect penis, and the penis positioned within the open end of a plastic cylinder of a vacuum erection device with the annular flange of the prosthesis compressed against the user's groin and resting tightly against the circumference of the open end of the cylinder.

Referring to FIGS. 37 and 41, vacuum tube 200 is pressed toward the user's groin 90 so that pubic shield 20 is squeezed tightly between the circumference of open end 202 and the user's groin 90. The outer surface 27 and the seating inner surface 26 of pubic shield 20 create an air-tight seal between vacuum tube 200 and penile prosthesis 10 drawing penis 50 further into chamber 206 and augmenting the user's erection. Note that the root 56 of the penis 50 is drawn further forward within penile prosthesis 10 without risk of drawing the patients' skin or scrotum inadvertently into the device. Physiologically, there is blood in the root 56 of the penis 50 posterior to the shield 20 of the prosthesis 10 even after the corpora cavernosa are filled by the pelvic exercises. The erection can be improved and maximized by the user using his fingers to press the shield 20 back against the pubic tissues and scrotum in a circular fashion to massage this blood through the prosthesis 10 and into the penis 50. This action also insures and reinforces the pressure of the dorsal ridge 32 against the dorsal penile veins 70 and 72, and this action pulls the root 56 of the penis 50 further into the vacuum chamber 206 and helps to elongate the penile shaft 52. Desirably, the entire length of the penis 50 from its glans 84 to its root 56 posterior to the prosthesis 10 may become rigid. In prior art constriction rings, refer to FIG. 25, which only fit over the base 54 of the penis and do not support the portion of the penis posterior to the device, this portion of the penis remains relatively flaccid. By contrast, in embodiments of prosthesis 10 as described herein, when the penis 50 is brought to the desired erect state, the vacuum within the chamber 206 is emptied, and erect penis 50 is removed while prosthesis 10 remains snugly positioned around the base 54 of penis 50 as shown in FIG. 38, while the user engages in the desired intimate activities.

In some embodiments, a penile prosthesis 10 may include a retention strap 300, as also described herein in reference to FIG. 39A and FIG. 39B, for example. Retention strap 300 may be made of a flexible or elastic material. Upon completion of the desired activities, prosthesis 10 may be removed by first sliding retention strap 300 from behind the scrotum 102, then collar 12 may be slid forward toward the glans penis 84. Contralateral edges 22 of shield 20 may be grasped and pulled apart by the user, thus widening channel 14 of collar 12, relieving pressure upon the dorsum of the penis in the region of the dorsal penile veins. This may be accompanied by rotation of the prosthesis 10 in order to ensure relief of compression of the veins and facilitate return of the erect penis to a flaccid state. Simultaneously, compression of dorsal penile veins 70 and 72 is relieved by removal of compressive action of dorsal ridge 32. As the penis 50 becomes flaccid, removal of the prosthesis 10 becomes easier. Water may be poured along the seating inner surface 26 and into the funnel-like opening 16 (see, e.g., FIG. 2) thus creating a slippery interface that aids in removal of the prosthesis 10.

FIG. 39A shows a penile prosthesis 10 according to some embodiments which includes a retention strap 300 connected to the periphery of pubic shield 20 of the prosthesis 10. The retention strap 300 may be integrally molded with the rest of the penile prosthesis 10. As shown in the exemplary embodiment of FIG. 39A, the retention strap 300 may have an essentially semicircular shape. Between the lower periphery of pubic shield 20 and retention strap 300 is an aperture 321 which is provided to encircle the user's scrotum 102 when the prosthesis 10 is used. The retention strap 300 may be formed of an elastic material that may be stretched substantially beyond its original length and when relaxed it may return to its original length.

The length of retention strap 300 may be around 7 cm, for example, and may be greater than the distance between connection points 302a and 302b. The unstretched length of retention strap 300 may be varied to accommodate different user's anatomy. Dotted line 300s and stretched aperture 321s depict a wide latitude of stretchability of strap 300 in order to accommodate a wide variety of anatomies for different users. Any suitable dimensions may be used.

In order to simplify the construction of penile prosthesis 10, the components may be integrally molded to include retention strap 300. In other embodiments, retention strap 300 may be made separately. Of course, the hardness and modulus of elasticity of strap 300 may be chosen to be different from the rest of pubic shield 20 in order for the strap 300 to provide appropriate elastic recoil and strength.

In some embodiments, the ends of retention strap 300 may be connected to connection points 302a and 302b along the periphery of pubic shield 20. Connection points 302a and 302b may be positioned opposite to each other relative to the aperture 321 such as below the level of channel 14 of collar 12 in order to bias the prosthesis 10 posteriorly and inferiorly upon stretching of strap 300 (see arrows 350).

Due to the arrangement of the elastic strap 300 with respect to channel 14, the channel's cross-sectional configuration may be deformed upon depression of connection points 302a and 302b as retention strap 300 is tensioned downward. As a result of tensioning of the retention strap 300, dorsal ridge 32 may be urged inwards into channel 14 as shown by arrow 352 compressing the dorsum of the penis within channel 14 thus augmenting compression of dorsal penile veins 70 and 72, pubic shield 20 may be forced downwards and backwards against the user's pubis causing a tighter fit of the device, or both. Additionally, in some embodiments, the deep penile veins at the underside surface at the root of the penis in the perineum behind the scrotum are simultaneously compressed by the strap 300 to ensure that all the draining veins of the penis are adequately compressed. These actions may help stabilize penile prosthesis 10 against forward slippage during sexual activity without the user's aid. Advantageously, in some embodiments, the fitting latitude of retention strap 300 may be widened thus promoting functionality and user's satisfaction. Downward bias of pubic shield 20 may depress ventral recess 34, thus relieving pressure upon the user's urethra by the ventral recess wall 42. In some embodiments, connection points 302a and 302b may be positioned at a horizontal line spaced at or below the level of ventral recess 34.

With reference to FIG. 39B, according to some embodiments, retention strap 300 may include a strap buckle 340 connected to a first strap portion 300a attached to the penile prosthesis 10 at a first connection point (e.g., connection point 302a as shown in FIG. 39A) and a second strap portion 300b attached to the penile prosthesis 10 at a second connection point (e.g., connection point 302b as shown in FIG. 39A). The strap buckle 340 may, for example, be adjustable and configured for quick and easy cinching and release. For example, buckle 340 may include a button 342 that may be pressed in order to allow the buckle 340 to slide forward with respect to the strap portions 300a and 300b and thereby cinch them up about the user's scrotum (e.g., while the user holds the ends 308a and 308b), and when the button 342 is released the buckle 340 may be held snugly in place with respect to the strap portions 300a and 300b. Similarly, button 342 may be pressed in order to slide buckle 340 backward with respect to the strap portions 300a and 300b and thereby loosen strap 300 for removal from the scrotum. In some embodiments, ends 308a and 308b of strap portions 300a and 300b may be loose ends, or ends 308a and 308b may be tied or otherwise fastened together, or strap portions 300a and 300b may be part of a continuous strap 300.

In one aspect, an external penile prosthesis retention strap may include two attachment portions connected by an adjustable length strap. The strap may be of a sufficient length to wrap around the user's scrotum, to secure an external penile prosthesis around the base of a user's penis. The strap may, in some cases, be sufficiently wide to reduce or prevent movement and/or rotation of the prosthesis. The strap may, in some cases, be sufficiently tightened by the user to generate enough tension to compress the deep veins behind the scrotum to eliminate venous insufficiency and maintain a strong erection. In some embodiments, the strap buckle 340 may be disposed between a second end of the first strap and a proximal end of a second strap for removably surrounding a user's scrotum.

Figure 40A:
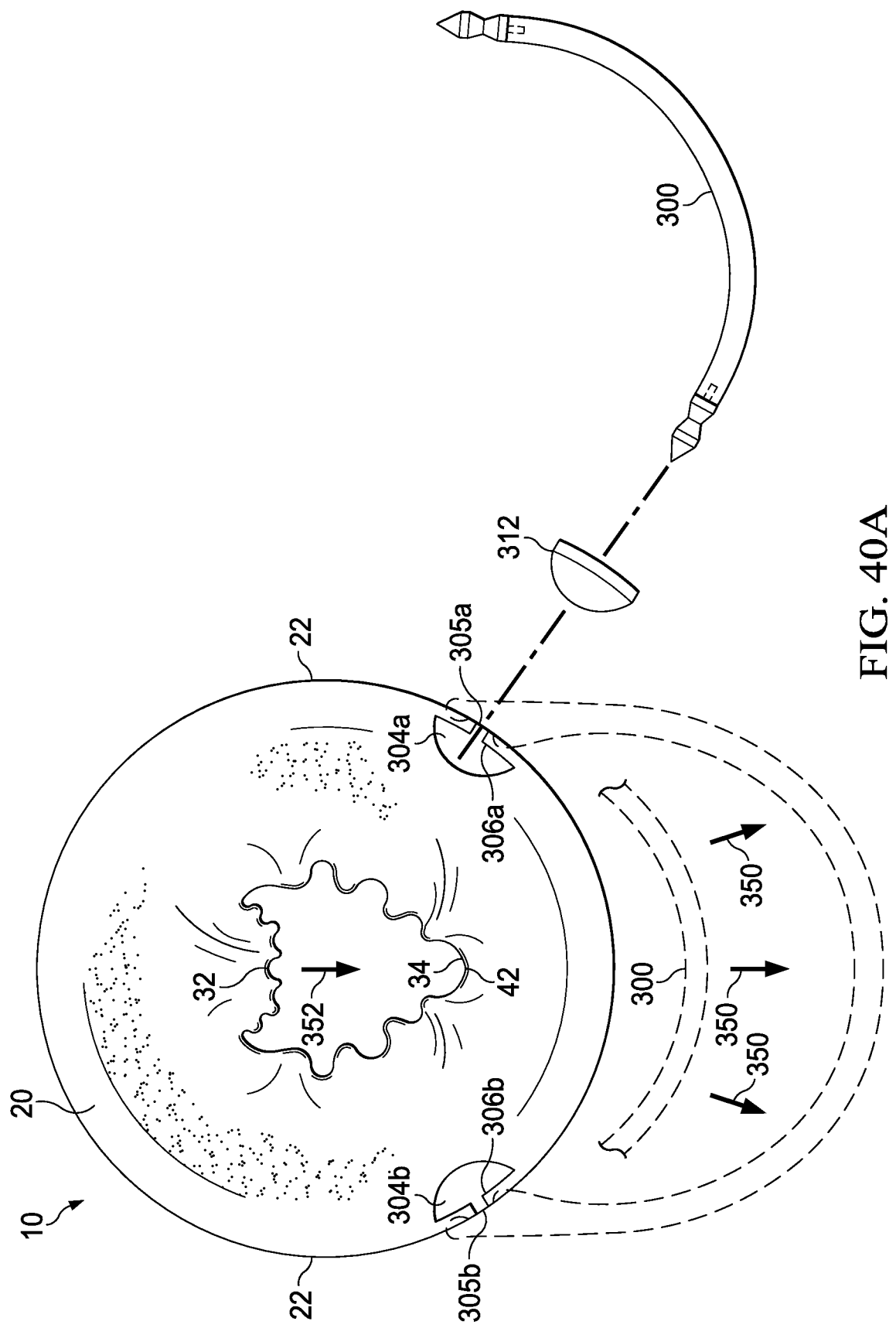
FIG. 40A is a view similar to FIG. 39A wherein the retention strap is manufactured separately and its two ends may be reversibly connectable to the periphery of the pubic shield.
Figure 40B:
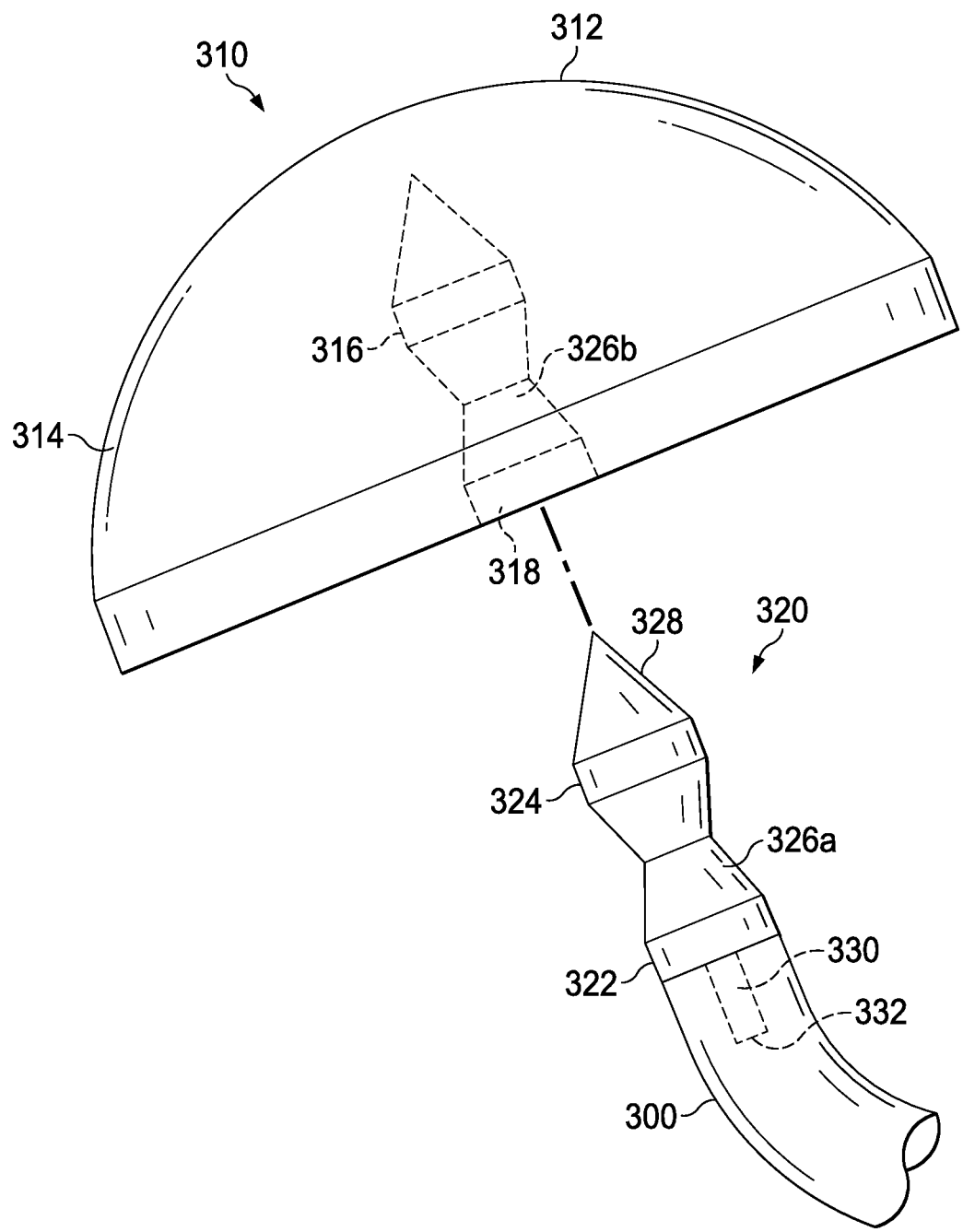
FIG. 40B is a perspective view of male and female components of a snap button assembly which is configured to fit snugly in a correspondingly shaped anchoring socket in the periphery of the pubic shield portion of the external penile prosthesis.

With reference now to FIGS. 40A and 40B, according to some embodiments, the elastic strap 300 may be formed and provided separately from pubic shield 20 in different lengths, diameters, cross-sectional configurations, and elastic strengths and moduli. The cross-sectional configuration of elastic strap 300 may be circular, oval, ovoid, or other suitable configuration, and may be about 5 mm in diameter and about 7-15 cm in unstretched length, for example. The ends of the strap may be reversibly connected and disconnected from pubic shield 20 at connection points 302a and 302b (see FIG. 39A). The pubic shield-collar structure may be molded of a polymer and may have a pair of anchoring sockets 304a and 304b arranged at connection points 302a and 302b. Anchoring sockets 304a and 304b may define annular spaces with relatively narrow central apertures 305a and 305b, and peripheral flanges 306a and 306b extending annularly in surrounding relation to the central apertures.

As shown in FIGS. 40A and 40B, a female component 312 (which may be one of a pair of female components, only one is shown for simplicity) of a snap button assembly 310 may be shaped and configured to complement the shape of one of anchoring sockets 304a and 304b, and may be of the same size or slightly larger than the sockets 304a or 304b. When a female component 312 is squeezed through central aperture 305a or 305b, and positioned within the annular space of one of the anchoring sockets 304a or 304b, it becomes entrapped therein by one of the peripheral flanges 306a or 306b, thus preventing its expulsion by pulling action of elastic strap 300. A bonding agent or glue, for example, may be used to hold the component 312 securely within the socket 304a or 304b. The female component 312 may include a deformable button body 314 and a fastener receiving aperture 318. The female component 312 may be adapted to retainingly receive the shank 324 of an associated male component 320 in an axial recess 316 through the fastener receiving aperture 318. When assembled, the fastener receiving aperture 318 of button body 314 may be easily identifiable along the edge of pubic shield 20. Button body 314 may be made of metal or synthetic polymer, for example, and may include a circular domed head having a central axial recess 316 accessible through the fastener receiving aperture 318.

As shown in FIG. 40B, male component 320 of snap button assembly 310 may be made of metal or preferably synthetic polymer and may include a circular base 322 and a central shank 324 projecting therefrom. The shank 324 may have a maximum diameter substantially equal to or slightly larger than the diameter of the fastener receiving aperture 318. The shank 324 may have a waist portion 326a disposed substantially centrally thereof and extending there around in tandem relation to a waist receiving portion 326b in the central axial recess 316 of button body 314. Male component 320 may terminate distally at a spear tip 328. The overall configuration of male component 320 may be designed and configured to fit snugly and firmly within central axial recess 316 in order to act as a clutch or locking mechanism to hold elastic strap 300 securely and detachably to pubic shield 20. Those with ordinary skill in the art will appreciate that other forms of snap button assemblies may be utilized, and other methods of reversible fastening of male fasteners within apertures of female button bodies may be utilized. Of course, any suitable means of fastening strap 300 to shield 20 may be used.

With further attention to FIG. 40B, a stem portion 330 may project perpendicularly centrally from the back face of circular base 322 contralateral to central shank 324. Stem 330 may be adapted for tight insertion and secure bonding within a corresponding recess 332 at one end of elastic strap 300. In some embodiments for assembly of penile prosthesis 10, shank 324 of male component 320 may be inserted through fastener receiving aperture 318 of button body 314 to which one end of elastic strap 300 is to be attached, and then shank 324 may be fitted forcibly into axial recess 316 in button body 314 until the components are tightly aligned so that a click is perceived, ensuring accurate alignment of waist portions 326a and 326b thus preventing male component 320 from being separated from button body 314 upon stretching of elastic strap 300.

FIG. 41 shows a conventional vacuum type penile erection device for a male penis 50 having a shaft portion 52, a base portion 54, a root portion 56, and a glans 84. The penile erection device includes a vacuum tube 200 into which the male penis 50 is inserted. A source of vacuum such as a hand or electric pump (not shown) for evacuating or removing air from tube 200 via flexible hose 204 is provided.

Vacuum tube 200 may be a conventional, generally cylindrical shaped transparent plastic tube having a distal end connected to a flexible hose 204 or to a mechanized battery-operated air pump, for example. Conventionally, the diameter of the tube 200 is about 2 inches. The tube 200 is rigid and maintains its shape when at least 24 inches of mercury or other suitable level of vacuum pressure is achieved inside the tube. An outwardly projecting lip 208 is formed around the circumference of the open proximal end of tube 200. The lip 208 may have a thickness of about 0.24 inch and its edges may be rounded for comfort and for forming an air-tight seal against the front surface of pubic shield 20 of penile prosthesis 10. The tube 200 may be sized to accommodate the genitalia of most male individuals.

Most commercially available vacuum erection devices utilize a diaphragm seal made of an integral piece of soft, flexible rubber to facilitate comfort and to create an air-tight fit against the user's pubis and around the user's penis. However, one shortcoming of such diaphragms is that they may not form a sufficiently air-tight seal to produce a desired amount of vacuum pressure inside the tube.

Conventional constriction rings used with such vacuum tubes and diaphragms are not designed to allow the root of the penis to be drawn into the constrictor ring (refer to FIG. 25). When the vacuum tube is removed, only that portion of the shaft of the penis anterior to the ring becomes erect, and the part of the penis behind the ring including the portion of the penis at the level of the scrotum does not become filled with pressurized blood and therefore does not become rigid. The base and root of the penis remain or return to a flaccid state, and the penis does not achieve and maintain a natural erect state.

Figure 42:
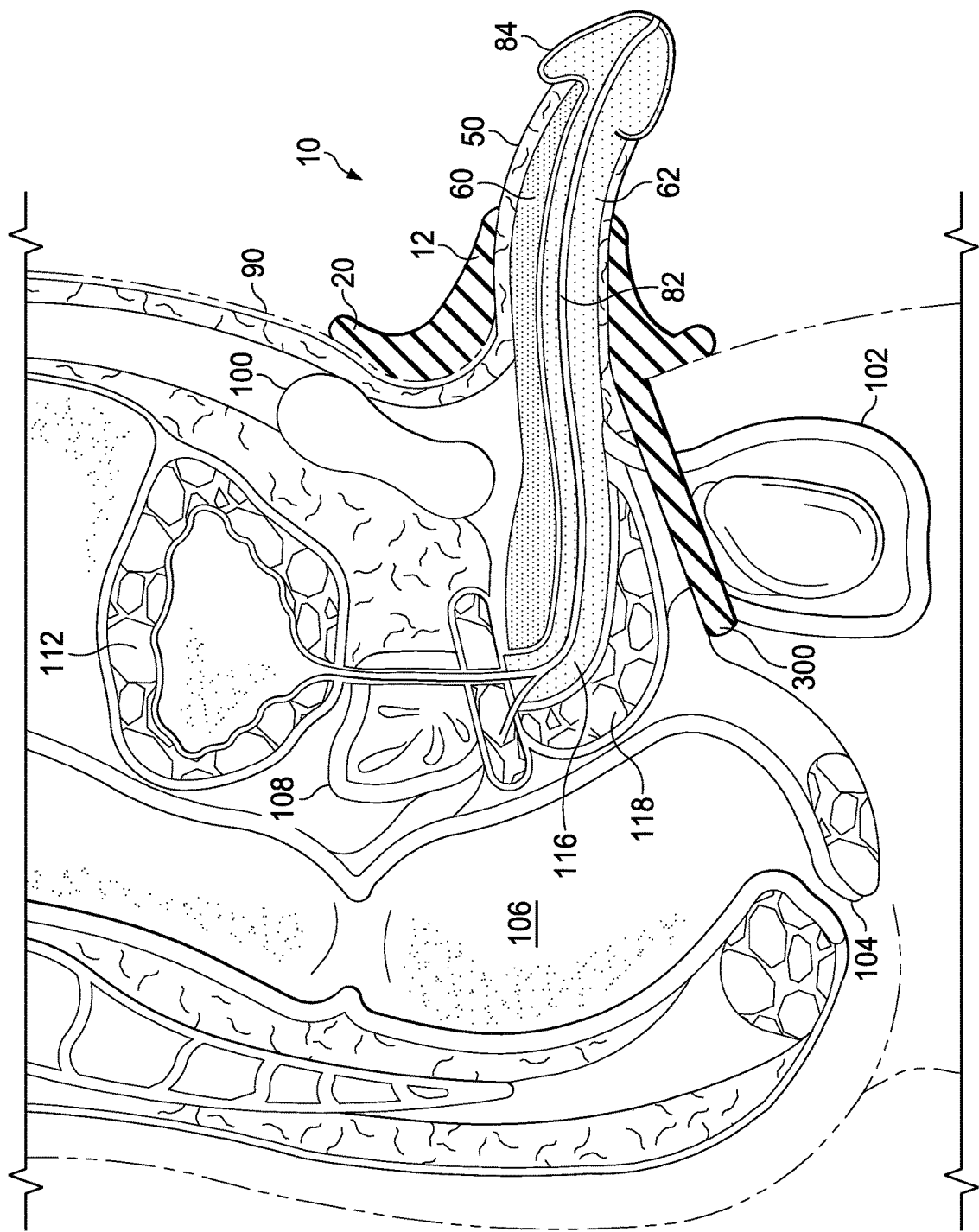
FIG. 42 is a sagittal anatomic cross-sectional view of the male human pelvis depicting major anatomic landmarks relative to an embodiment of the present invention. An external penile prosthesis including a retention strap has been superimposed to demonstrate the position of the prosthesis including the retention strap with respect to the user's penis and scrotum.

FIG. 42 illustrates certain basic anatomical landmarks of the human male pelvis in relation to an embodiment of a penile prosthesis 10 as described herein: pubic bone 100, scrotum 102, anus 104, rectum 106, prostate gland 108, glans penis 84, bulbous spongiosum 116, corpus cavernosus 60, urinary bladder 112, urethra 82, corpus spongiosum 62, and pubococcygeous (PC) muscle and/or the levator ani muscle 118.

When an external penile prosthesis 10 as described herein is used with a simple vacuum tube (as shown in FIG. 41 for example), without the aid of a diaphragm, a complete air-tight state is achieved due to compression of the front face 27 of pubic shield 20 against lip 208 of vacuum tube 200.

Referring again to FIG. 42, the prosthesis 10 is designed for facilitating unhindered flow of blood into the entire penis 50 while selectively obstructing venous return from the dorsal penile veins and the deep veins behind the scrotum 102. When the prosthesis 10 is positioned properly as shown in FIG. 42, including placement of elastic strap 300 behind the scrotum 102, the user is encouraged to perform repeated voluntary contractions of his pelvic muscles including the pubococcygeous (PC muscle), and/or the levator ani muscle 118. This action potentiates venous engorgement of the entire penis 50 including the portions in front of and behind the prosthesis 10. Contraction of the muscle also compresses the urethra 82 (when one desires to interrupt urination temporarily). As advised by erectile dysfunction specialists, contracting this muscle repeatedly several times per day or on a daily basis strengthens the muscle and improves its physiologic health. This exercise may have the added benefit of controlling the condition of overactive bladder. The PC muscle in both the male and female runs between the pubic bone 100 in front and the coccyx (tail bone) in the back. Voluntary tensioning of this muscle by the user, especially when using the prosthesis 10 during evacuation pumping by a vacuum erection device, can increase blood flow in the deep part of the penis 50 behind the prosthesis 10 as well as in front of the prosthesis 10 into the visible erect shaft 52 of the penis 50. Exercises for toning these muscles are known as Kegel exercises. Cyclically tensing and relaxing of these muscles by the user while wearing the device of the invention and while the user's penis 50 is in full erection, on a daily basis, can improve blood flow into the penis 50, especially when this routine is performed with or without coitus.

All patents and published patent applications referenced in this disclosure are incorporated herein by reference.

While the apparatus of the invention is described herein in relation to exemplary embodiments, it is understood that other alterations and modifications of the invention will become apparent to those of ordinary skill in the art upon reading this disclosure, and it is intended that the scope of the invention be limited only to the broadest interpretation of the appended claims to which the inventor is legally entitled.

The embodiments described herein are some examples of the current invention. It will be appreciated by those skilled in the art that changes could be made to the embodiments and features described above without departing from the broad inventive concept thereof. It is understood, therefore, that this invention is not limited to the particular embodiments disclosed, but it is intended to cover modifications within the spirit and scope of the present invention. Among other things, any feature described for one embodiment may be used in any other embodiment. Also, unless the context indicates otherwise, it should be understood that when a component is described herein as being mounted or connected to another component, such mounting or connection may be direct with no intermediate components or indirect with one or more intermediate components. The scope of the invention is defined by the attached claims and other claims that may be drawn to this invention, considering the doctrine of equivalents, and is not limited to the specific examples described herein.

What is claimed is:

1. An external penile prosthesis adapted for use in the treatment of erectile dysfunction of a user, the user having a pubis, a scrotum, and a penis including a shaft, a base of the shaft, a top side, an underside, a glans, a urethra, a superficial dorsal vein, a deep dorsal vein, arteries, nerves, corpora cavernosa, and corpus spongiosum, the prosthesis comprising:

a collar having a central channel that is contractible to accommodate the user's penis in a flaccid state and expandable to accommodate the user's penis in an erect state, said central channel comprising a dorsal ridge and a ventral recess, wherein said channel is defined by a wall of generally trefoil configuration that includes said dorsal ridge contralateral to said ventral recess, a pair of dorsolateral recesses bordering said dorsal ridge, and at least two sets of arcuate ribs disposed longitudinally along sidewalls of said channel; and a pubic shield extending radially from said collar at a proximal end of said collar, said shield having a rearward facing surface conformable to the user's pubis;
wherein said dorsal ridge is configured in a substantially wedge-shape and smoothly rounded to reversibly compress the superficial dorsal vein and the deep dorsal vein of the penis and to distract and substantially avoid compression of the arteries and nerves; and
wherein said ventral recess is configured to substantially avoid compression of the urethra.

2. The prosthesis of claim 1, wherein said collar is elongate and said channel has a funnel-like configuration at its proximal end configured for receiving the glans of the user's penis.

3. The prosthesis of claim 1, wherein said collar has a length and an unexpanded outer diameter, said length ranging from about 25 mm to about 50 mm, and said unexpanded outer diameter ranging from about 20 mm to about 35 mm.

4. The prosthesis of claim 1, wherein said collar is substantially frustoconical.

5. The prosthesis of claim 1, wherein the prosthesis is molded from one or more thermoplastic polymeric materials in a unitary construction operation.

6. The prosthesis of claim 1, wherein said collar has a generally trefoil unexpanded cross-sectional shape.

7. The prosthesis of claim 6, wherein said collar has a wall of variable thickness that generally tapers from its proximal end to its distal end.

8. The prosthesis of claim 7, wherein stretchability of said collar increases from its proximal end to its distal end.

9. The prosthesis of claim 1, wherein said channel has an unexpanded proximal diameter of about 30-40 mm and an unexpanded distal diameter of about 17-22 mm.

10. The prosthesis of claim 1, wherein said channel has a circumference that decreases from its proximal end to its distal end.

11. The prosthesis of claim 1, wherein said channel comprises a proximal opening that is substantially funnel-shaped and is sized and shaped to provide a tight fit and an airtight seal to the glans of the user's flaccid penis upon insertion of the penis into the prosthesis.

12. The prosthesis of claim 1, wherein said collar comprises a smoothly tapered distal end that is shaped and configured to present a comfortable and safe edge against tissues of the user and a sexual partner of the user.

13. The prosthesis of claim 1, wherein said channel has a longitudinal axis that is substantially perpendicular to the shield.

14. The prosthesis of claim 1, wherein said channel has a longitudinal axis that is angled to the right or to the left of the shield.

15. The prosthesis of claim 1, wherein said channel has a longitudinal axis that is angled cephalad with respect to the shield.

16. The prosthesis of claim 1, wherein said collar has an unexpanded length and an unexpanded outer diameter, the unexpanded length ranging from about 1.2 to about 1.7 times the unexpanded outer diameter.

17. The prosthesis of claim 1, wherein said collar has an unexpanded length and an unexpanded outer diameter, the unexpanded length and the unexpanded outer diameter being about equal.

18. The prosthesis of claim 1, wherein said shield has a uniform thickness of about 7-8 mm.

19. The prosthesis of claim 1, wherein said shield has a diameter of about 60-80 mm.

20. The prosthesis of claim 1, wherein, in an unexpanded state, said shield extends radially about 20 mm from said collar to an edge of said shield.

21. The prosthesis of claim 1, wherein the collar is integral with the shield, the shield comprising a sloping shoulder, the shoulder being configured so that an outer surface of the collar merges smoothly with an outer surface of the shield.

22. The prosthesis of claim 1, wherein said shield comprises a forward-facing sealing surface configured to form an air-tight interface with a front edge of a vacuum cylinder.

23. The prosthesis of claim 1, wherein said collar and said shield are unitarily molded from one or more thermoset polymeric materials.

24. The prosthesis of claim 1, wherein said dorsal ridge projects inwardly from a roof of said channel to thereby exert inward pressure on the dorsal veins near the user's pubis.

25. The prosthesis of claim 1, wherein said dorsal ridge has a thickness greater than other portions of said collar.

26. The prosthesis of claim 1, wherein said ventral recess is defined by a ventral recess wall that is thinner and more elastic than said sidewalls of said collar.

27. The prosthesis of claim 26, wherein said ventral recess is sufficiently wide to accommodate the user's urethra and said ventral recess wall is sufficiently firm to prevent compression of the user's urethra and to allow differential stretching of the sidewalls of the collar to accommodate expansion of the channel by the user's erect penis.

28. The prosthesis of claim 1, wherein said prosthesis comprises an elastomeric material and is configured for improving an erection of the penis by means of deliberately choking backflow of venous blood in the dorsal penile veins and sparing the penile arteries, nerves, urethra, corpora cavernosa, and corpus spongiosum.

29. The prosthesis of claim 1, wherein said collar and said shield are made of a single material and said sidewalls are thinner than a top wall comprising said dorsal ridge.

30. The prosthesis of claim 1, wherein said channel comprises sidewalls configured to stretch, grab, and support the base of the penile shaft in an erect state.

31. The prosthesis of claim 1, wherein said collar has an outer surface that is smooth, slippery, and non-wettable.

32. The prosthesis of claim 1, wherein said shield comprises an elastomer, wherein at least a portion of said rearward facing surface is textured such as to give said rearward facing surface an improved characteristic as compared to a surface of said elastomer that is not textured, wherein the characteristic is selected from the group consisting of improved dry skin lubricity, improved damp skin lubricity, increased comfort, and decreased skin irritation.

33. The prosthesis of claim 1, wherein at least a portion of said rearward facing surface is given a texture during a molding process.

34. The prosthesis of claim 1, wherein said collar comprises an elongate body comprising a first sidewall having a first profile and a second sidewall disposed at a substantially 60 degree angle opposite the first sidewall, the second sidewall having a second profile different from the first profile such that expansion of the collar causes the elongate body to bend.

35. The prosthesis of claim 1, wherein said collar comprises sidewalls having an elasticity greater than that of the dorsal ridge.

36. The prosthesis of claim 1, wherein the dorsal ridge is substantially nondistensible and formed from a polymer selected from the group consisting of silicone, nylon, propylene, polyimide, polyethylene, polypropylene, and polyether ether ketone.

37. The prosthesis of claim 1, wherein the shield is formed from a forward facing layer and a rearward facing layer, wherein the forward facing layer extends anteriorly to form an outer layer of said collar, and the rearward facing layer extends anteriorly to form an inner layer of said collar.

38. The prosthesis of claim 37, wherein said collar and said shield are made of the same polymer material, and said outer layer is made of a lower hardness material than said inner layer.

39. The prosthesis of claim 1, wherein the sidewalls are formed from a polymer selected from the group consisting of silicone, latex, neoprene, silastic, chronoprene, siloxane, and polyether block amide.

40. The prosthesis of claim 1, wherein the dorsal ridge is formed from a material with a higher hardness compared to that of other portions of the collar.

41. The prosthesis of claim 1, wherein the dorsal ridge comprises a silicone polymer having a hardness of about Shore 20.

42. The prosthesis of claim 1, wherein some portions of said collar have different flexibility, hardness, and modulus of elasticity.

43. The prosthesis of claim 1 further comprising a strap extending from said shield and being positionable about the user's scrotum along the underside of the user's penis.

44. The prosthesis of claim 43, wherein said strap is configurable such that the prosthesis compresses veins behind the scrotum, pulls the collar downward to enhance compression of the dorsal veins, and relieves pressure on the urethra.

45. The prosthesis of claim 43, wherein said strap comprises a first strap portion and a second strap portion joined by a buckle, wherein said buckle is adjustable for tightening and loosening said strap.

46. The prosthesis of claim 1, further comprising an elastic strap adapted to surround the underside of the user's penis behind the scrotum, said strap being a resilient retention strap having one end portion disposed at a periphery of said pubic shield at a first location and having another end portion disposed at the periphery of said pubic shield at a second location spaced from said first location.

47. The prosthesis of claim 46, wherein said elastic strap is formed integrally with said pubic shield.

48. The prosthesis of claim 46, wherein said elastic strap is formed separately from said pubic shield.

49. The prosthesis of claim 48, wherein said pubic shield comprises a pair of contralateral anchoring sockets at its periphery, said sockets being shaped and configured to receive ends of said elastic strap for reversible attachment of said elastic strap to said shield.

50. The prosthesis of claim 49, wherein said shield comprises a pair of snap button assemblies shaped and configured for reversible attachment of ends of said elastic strap to corresponding connection points at said anchoring sockets at the periphery of said pubic shield.

51. The prosthesis of claim 46, wherein said elastic strap comprises at least one of a length, diameter, cross-sectional configuration, and elastic modulus to insure that said prosthesis is secured in position while in use by the user.

52. The prosthesis of claim 46, wherein said elastic strap is configured to depress said pubic shield to draw the dorsal ridge against the top side of the user's penis and compress the dorsal penile veins.

53. The prosthesis of claim 46, wherein said elastic strap is configured to depress the pubic shield thereby relieving compression of the urethra in the region of the ventral recess.

54. The prosthesis of claim 46, wherein said elastic strap is configured to surround the underside of the user's penis behind the scrotum thereby compressing the deep penile veins causing obstruction of venous outflow to maintain erection of the user's penis.

55. A method of using the penile prosthesis of claim 1 with a vacuum erection device which comprises a vacuum cylinder with an open end, the shield of the prosthesis having a forward-facing sealing surface, the collar of the prosthesis having a funnel-like front aperture, the method comprising:
- placing the penile prosthesis over the open end of the vacuum cylinder so that the sealing surface of said shield rests flush against the open end of the vacuum cylinder thereby forming an airtight seal between said shield and the vacuum cylinder;
- placing the user's flaccid penis into the funnel-like front aperture of said penile prosthesis thereby creating a seal between the user's penis and the penile prosthesis;
- operating said vacuum erection device to draw said penis into the cylinder;
- further activating the vacuum within the cylinder gradually while the user performs Kegel or pelvic contraction exercises until said penis is in the desired erect state;
- pressing said vacuum cylinder against the pubic shield, driving the shield towards the user's groin, stabilizing the root of the penis and driving the user's penis forward and deeper into the cylinder, thus maximizing erection of the penis;
- releasing the vacuum within the cylinder; and
- removing the erect penis from the cylinder with the prosthesis disposed about the penis.

* * * * *